US007026635B2

(12) United States Patent

Rangwalla et al.

(10) Patent No.: US 7,026,635 B2

(45) Date of Patent: *Apr. 11, 2006

(54) PARTICLE BEAM PROCESSING APPARATUS AND MATERIALS TREATABLE USING THE APPARATUS

(75) Inventors: Imtiaz Rangwalla, Andover, MA (US); Harvey Clough, Derry, NH (US); George Hannafin, Hudson, NH (US)

(73) Assignee: Energy Sciences, Wilmington, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/631,678

(22) Filed: Jul. 31, 2003

(65) Prior Publication Data

US 2004/0089820 A1 May 13, 2004

Related U.S. Application Data

(63) Continuation of application No. PCT/US03/23731, filed on Jul. 30, 2003, and a continuation-in-part of application No. 10/153,622, filed on May 24, 2002, which is a continuation-in-part of application No. 09/434,380, filed on Nov. 5, 1999, now Pat. No. 6,426,507.

(51) Int. Cl.

*A61N 5/00* (2006.01)
*G21G 5/00* (2006.01)
*H05H 7/00* (2006.01)

(52) U.S. Cl. .................. 250/492.3; 250/435; 250/398; 315/506; 313/420

(58) Field of Classification Search ............ 250/492.3, 250/442.3, 435, 398; 428/345, 411.1, 500; 313/361.1, 420; 315/506

See application file for complete search history.

(56) References Cited

U.S. PATENT DOCUMENTS

| | | | | |
|---|---|---|---|---|
| 1,272,004 | A | 7/1918 | Campbell | |
| 1,275,904 | A | 8/1918 | Grotta | |
| 2,008,361 | A | 7/1935 | Lindsey | 229/51 |
| 2,079,328 | A | 5/1937 | McBean | 229/51 |
| 2,140,748 | A | 12/1938 | Johanson | 229/87 |
| 2,301,997 | A | 11/1942 | Basilone et al. | 229/87 |
| 3,106,333 | A | 10/1963 | Bulovic | 229/87 |
| 3,237,843 | A | 3/1966 | Reed et al. | 229/51 |

(Continued)

FOREIGN PATENT DOCUMENTS

EP 0 339 670 A2 11/1989

(Continued)

OTHER PUBLICATIONS

Copy of the International Search Report issued in related application PCT/US03/23731.

(Continued)

*Primary Examiner*—John R. Lee
*Assistant Examiner*—Johnnie L Smith, II
(74) *Attorney, Agent, or Firm*—Finnegan, Henderson, Farabow, Garrett & Dunner, L.L.P.

(57) ABSTRACT

Methods, and materials made by the methods, are provided herein for treating materials with a particle beam processing device. According to one illustrative embodiment, a method for treating a material with a particle beam processing device is provided that includes: providing a particle beam generating assembly including at least one filament for creating a plurality of particles; applying an operating voltage greater than about 110 kV to the filament to create the plurality of particles; causing the plurality of particles to pass through a thin foil having a thickness of about 10 microns or less; and treating a material with the plurality of particles.

23 Claims, 13 Drawing Sheets

U.S. PATENT DOCUMENTS

| | | | | |
|---|---|---|---|---|
| 3,440,466 | A | 4/1969 | Colvin et al. | 313/35 |
| 3,832,827 | A | 9/1974 | Lemelson | 53/111 R |
| 3,865,664 | A | 2/1975 | Neumann | 156/192 |
| 3,925,670 | A | 12/1975 | Farrell | 250/400 |
| 4,070,262 | A | 1/1978 | Guarino et al. | 204/159.24 |
| 4,071,425 | A | 1/1978 | Guarino et al. | 204/159.24 |
| 4,072,592 | A | 2/1978 | Due et al. | 204/159.15 |
| 4,082,594 | A | 4/1978 | Stonehouse | 156/253 |
| 4,143,468 | A | 3/1979 | Novotny et al. | 34/1 |
| 4,210,813 | A | 7/1980 | Romanovsky et al. | 250/421 |
| 4,246,297 | A | 1/1981 | Nablo et al. | 427/44 |
| 4,246,315 | A | 1/1981 | Kopp et al. | 428/315 |
| 4,248,665 | A | 2/1981 | Thode | 176/1 |
| 4,288,479 | A | 9/1981 | Brack | 428/40 |
| 4,323,780 | A | 4/1982 | Tombaugh et al. | 250/419 |
| 4,323,858 | A | 4/1982 | Gerstley | 372/107 |
| 4,324,980 | A | 4/1982 | Symmons | 250/505 |
| 4,330,590 | A | 5/1982 | Vesley | 428/336 |
| 4,381,322 | A | 4/1983 | Bahr et al. | 427/179 |
| 4,384,026 | A | 5/1983 | Moore et al. | 428/412 |
| 4,446,374 | A | 5/1984 | Ivanov et al. | 250/492.3 |
| 4,490,409 | A | 12/1984 | Nablo | 427/44 |
| 4,501,797 | A | 2/1985 | Super et al. | 428/349 |
| 4,507,614 | A | 3/1985 | Prono et al. | 328/233 |
| 4,522,887 | A | 6/1985 | Koebisu | 428/461 |
| 4,537,811 | A | 8/1985 | Nablo | 428/166 |
| 4,577,205 | A * | 3/1986 | Shibata et al. | 503/204 |
| 4,589,145 | A | 5/1986 | Van Erden et al. | 383/5 |
| 4,594,262 | A | 6/1986 | Kreil et al. | 427/44 |
| 4,654,379 | A | 3/1987 | Lapin | 522/15 |
| 4,658,963 | A | 4/1987 | Jud | 206/632 |
| 4,714,655 | A | 12/1987 | Bordoloi et al. | 428/345 |
| 4,720,416 | A | 1/1988 | Duncan | 428/195 |
| 4,777,077 | A | 10/1988 | Miyazawa et al. | 428/200 |
| 4,786,552 | A | 11/1988 | Sasaki et al. | 428/355 |
| 4,810,745 | A | 3/1989 | Pike et al. | 524/516 |
| 4,814,215 | A | 3/1989 | Lautenschlaeger et al. | 428/40 |
| 4,833,122 | A | 5/1989 | Doll et al. | 503/226 |
| 4,844,764 | A | 7/1989 | Nablo et al. | 156/275.5 |
| 4,845,370 | A | 7/1989 | Thompson et al. | 250/492.3 |
| 4,851,459 | A | 7/1989 | Ramalingam | 523/414 |
| 4,859,521 | A | 8/1989 | Pike et al. | |
| 4,889,884 | A | 12/1989 | Dust et al. | 524/314 |
| 4,898,787 | A | 2/1990 | Min et al. | 428/480 |
| 4,902,370 | A | 2/1990 | Dust et al. | 156/327 |
| 4,908,274 | A | 3/1990 | Jachmann et al. | 428/452 |
| 4,948,604 | A | 8/1990 | Kuehne et al. | 426/107 |
| 4,952,814 | A | 8/1990 | Huntzinger | 250/505.1 |
| 5,001,002 | A | 3/1991 | Gribbin et al. | 428/245 |
| 5,028,480 | A | 7/1991 | Dean | 428/314.4 |
| 5,030,302 | A | 7/1991 | Jud et al. | 156/164 |
| 5,048,260 | A | 9/1991 | Raymond et al. | 53/370.8 |
| 5,051,600 | A | 9/1991 | Schuetz et al. | 250/492.3 |
| 5,071,686 | A | 12/1991 | Genske et al. | 428/35.7 |
| 5,084,317 | A | 1/1992 | Epple | 428/40 |
| 5,085,906 | A | 2/1992 | Ast et al. | 428/36.92 |
| 5,085,939 | A | 2/1992 | Wenz et al. | 428/411.1 |
| 5,175,436 | A | 12/1992 | Puumalainen | 250/493.1 |
| 5,200,463 | A | 4/1993 | Flakus | 524/591 |
| 5,227,240 | A | 7/1993 | Tilley et al. | 428/412 |
| 5,258,225 | A | 11/1993 | Katsamberis | 428/331 |
| 5,266,400 | A | 11/1993 | Yarusso et al. | 428/345 |
| 5,268,230 | A | 12/1993 | Edwards | 428/409 |
| 5,271,968 | A | 12/1993 | Coyle et al. | 427/558 |
| 5,333,439 | A | 8/1994 | Bozich et al. | 53/450 |
| 5,376,388 | A | 12/1994 | Meyers | 426/5 |
| 5,392,592 | A | 2/1995 | Bozich et al. | 53/440 |
| 5,416,440 | A | 5/1995 | Lyons et al. | 315/500 |
| 5,426,131 | A | 6/1995 | Katsamberis | 522/16 |
| 5,431,763 | A | 7/1995 | Bradshaw | 156/256 |
| 5,434,010 | A | 7/1995 | Smith et al. | 428/520 |
| 5,436,073 | A | 7/1995 | Williams et al. | 428/343 |
| 5,445,867 | A | 8/1995 | Ogawa et al. | 428/195 |
| 5,455,105 | A | 10/1995 | Coyle et al. | 428/215 |
| 5,468,542 | A | 11/1995 | Crouch | 428/215 |
| 5,482,780 | A | 1/1996 | Wilkie et al. | 428/515 |
| 5,486,426 | A | 1/1996 | McGee et al. | 428/516 |
| 5,489,783 | A * | 2/1996 | Kristiansson | 250/492.3 |
| 5,527,578 | A | 6/1996 | Mazurek et al. | 428/41.8 |
| 5,530,255 | A | 6/1996 | Lyons et al. | 250/492.3 |
| 5,540,916 | A | 7/1996 | Parks et al. | 424/76.1 |
| 5,548,005 | A | 8/1996 | Kurth et al. | 523/414 |
| 5,561,298 | A | 10/1996 | Cirlin et al. | 250/432 R |
| 5,562,985 | A | 10/1996 | Sano et al. | 428/195 |
| 5,562,994 | A | 10/1996 | Abba et al. | 428/464 |
| 5,567,773 | A | 10/1996 | McGee et al. | 525/221 |
| 5,582,342 | A | 12/1996 | Jud | 229/87.05 |
| 5,603,972 | A | 2/1997 | McFarland | 426/240 |
| 5,604,041 | A | 2/1997 | Choi | 428/473.5 |
| 5,614,297 | A | 3/1997 | Velazquez | 428/218 |
| 5,616,400 | A | 4/1997 | Zhang | 428/195 |
| 5,626,966 | A | 5/1997 | Külper et al. | 428/423.1 |
| 5,650,453 | A | 7/1997 | Eckberg et al. | 522/31 |
| 5,671,882 | A | 9/1997 | Cerwinski et al. | 229/87.08 |
| 5,674,626 | A | 10/1997 | Khatib et al. | 428/447 |
| 5,676,785 | A | 10/1997 | Samonides | 156/244.11 |
| 5,691,022 | A | 11/1997 | Knauf | 428/40.1 |
| 5,691,052 | A | 11/1997 | Jones | 428/355 |
| 5,693,385 | A | 12/1997 | Parks | 428/34.2 |
| 5,725,909 | A | 3/1998 | Shaw et al. | 427/412.1 |
| 5,725,958 | A | 3/1998 | Matsuda et al. | |
| 5,741,505 | A | 4/1998 | Beyer et al. | 424/439 |
| 5,757,152 | A | 5/1998 | Yuem et al. | 428/323 |
| 5,783,266 | A | 7/1998 | Gehrke | 428/34.3 |
| 5,792,296 | A | 8/1998 | Soltysiak | 156/184 |
| 5,798,174 | A | 8/1998 | Wilkie | 428/347 |
| 5,801,387 | A | 9/1998 | Nablo et al. | 250/492.3 |
| 5,804,301 | A | 9/1998 | Curatolo | 428/352 |
| 5,804,610 | A | 9/1998 | Hamer et al. | 522/182 |
| 5,817,402 | A | 10/1998 | Miyake et al. | 428/159 |
| 5,827,615 | A | 10/1998 | Touhsaent et al. | 428/436 |
| 5,843,547 | A * | 12/1998 | Kulper et al. | 428/40.1 |
| 5,851,610 | A | 12/1998 | Ristey et al. | 428/34.9 |
| 5,859,521 | A | 1/1999 | Tajima et al. | 428/195 |
| 5,874,164 | A | 2/1999 | Caldwell | 428/306.6 |
| 5,885,630 | A | 3/1999 | Zurawski et al. | 426/5 |
| 5,888,649 | A | 3/1999 | Curatolo | 428/352 |
| 5,898,261 | A | 4/1999 | Barker | 313/420 |
| 5,904,973 | A | 5/1999 | Coward et al. | 428/198 |
| 5,932,298 | A | 8/1999 | Moon | 427/496 |
| 5,935,686 | A | 8/1999 | Daelmans et al. | 428/194 |
| 5,939,205 | A | 8/1999 | Yokoyama et al. | 428/474.4 |
| 5,945,174 | A | 8/1999 | Shaw et al. | 427/509 |
| 5,945,183 | A | 8/1999 | Johnson | 428/34.9 |
| 5,959,003 | A | 9/1999 | Lo et al. | 523/201 |
| 5,959,020 | A | 9/1999 | Oliveri et al. | 524/487 |
| 5,962,995 | A | 10/1999 | Avnery | 315/506 |
| 5,976,297 | A | 11/1999 | Oka et al. | 156/241 |
| 5,981,047 | A | 11/1999 | Wilkie | 428/215 |
| 5,981,650 | A | 11/1999 | Zhao et al. | 524/591 |
| 5,984,363 | A | 11/1999 | Dotson et al. | 283/61 |
| 5,985,426 | A | 11/1999 | Wilkie | 428/215 |
| 5,989,377 | A | 11/1999 | Wilheim et al. | 156/230 |
| 5,990,234 | A | 11/1999 | Stahovic et al. | 524/839 |
| 5,993,960 | A | 11/1999 | Nakayama et al. | 428/345 |
| 6,000,726 | A | 12/1999 | Campbell | 283/81 |
| 6,001,397 | A | 12/1999 | Boyd et al. | 426/5 |
| 6,007,666 | A | 12/1999 | Bunch et al. | 156/280 |
| 6,010,724 | A | 1/2000 | Boyd et al. | 426/5 |
| 6,022,612 | A | 2/2000 | Wilkie | 428/215 |
| 6,025,059 | A | 2/2000 | McGee et al. | 428/219 |
| 6,027,793 | A | 2/2000 | Lohwasser et al. | 428/216 |
| 6,071,585 | A | 6/2000 | Roth | 428/41.8 |
| 6,099,927 | A | 8/2000 | Freedman | 428/40.1 |

| | | | | |
|---|---|---|---|---|
| 6,100,357 | A | 8/2000 | Smith et al. | 526/348 |
| 6,106,761 | A | 8/2000 | Sjöberg et al. | 264/492 |
| 6,110,318 | A | 8/2000 | Goodman | 156/272.2 |
| 6,125,563 | A | 10/2000 | Girerd | 40/310 |
| 6,150,035 | A | 11/2000 | DeFife et al. | 428/500 |
| 6,197,909 | B1 | 3/2001 | Smith et al. | 526/348.1 |
| 6,210,517 | B1 * | 4/2001 | Eadara et al. | 156/273.3 |
| 6,218,004 | B1 | 4/2001 | Shaw et al. | 428/336 |
| 6,228,314 | B1 | 5/2001 | Trueblood et al. | 264/485 |
| 6,241,289 | B1 | 6/2001 | Külper et al. | 283/86 |
| 6,265,032 | B1 | 7/2001 | Kurose et al. | 427/547 |
| 6,287,613 | B1 | 9/2001 | Childress et al. | 426/129 |
| 6,294,249 | B1 * | 9/2001 | Hamer et al. | 428/345 |
| 6,309,724 | B1 | 10/2001 | Külper et al. | 428/40.1 |
| 6,329,465 | B1 | 12/2001 | Takahashi et al. | 525/191 |
| 6,337,113 | B1 | 1/2002 | Muggli et al. | 428/35.2 |
| 6,342,273 | B1 | 1/2002 | Handels et al. | 427/475 |
| 6,426,507 | B1 * | 7/2002 | Rangwalla et al. | 250/492.3 |
| 6,436,498 | B1 | 8/2002 | Rangwalla et al. | 428/35.7 |
| 6,458,430 | B1 | 10/2002 | Bernstein et al. | 427/525 |
| 6,504,163 | B1 | 1/2003 | Takayama et al. | 250/492.3 |
| 6,528,127 | B1 | 3/2003 | Edlein et al. | 427/494 |
| 6,545,398 | B1 * | 4/2003 | Avnery | 313/361.1 |
| 6,610,376 | B1 * | 8/2003 | Rangwalla et al. | 427/596 |
| 2002/0009553 | A1 | 1/2002 | Lutz | 427/552 |
| 2002/0100194 | A1 | 8/2002 | Huffer et al | 40/310 |
| 2002/0106465 | A1 | 8/2002 | Huffer et al. | 428/35.2 |
| 2002/0146525 | A1 | 10/2002 | Huffer et al. | 428/35.3 |
| 2003/0001108 | A1 * | 1/2003 | Rangwalla et al. | 250/492.3 |

FOREIGN PATENT DOCUMENTS

| | | | |
|---|---|---|---|
| EP | 0 502 330 | A2 | 9/1992 |
| EP | 0737593 | A2 | 10/1995 |
| EP | 0726162 | A1 | 8/1996 |
| EP | 1 219 463 | A2 | 7/2002 |
| GB | 156 362 | A | 10/1985 |
| WO | WO 90/06265 | | 6/1990 |
| WO | WO 91/05706 | | 5/1991 |
| WO | 98/29895 | A1 | 7/1998 |
| WO | WO 00/35671 | | 6/2000 |
| WO | WO 00/53429 | | 9/2000 |
| WO | WO 01/94451 | A2 | 12/2001 |
| WO | WO 01/94451 | A3 | 12/2001 |

OTHER PUBLICATIONS

Copy of the International Search Report issued in related application PCT/US03/16457.

* cited by examiner

PARTICLE BEAM PROCESSING APPARATUS AND MATERIALS TREATABLE USING THE APPARATUS

CROSS REFERENCE TO RELATED APPLICATIONS

This application is a continuation of PCT Application No. PCT/US03/23731 filed Jul. 30, 2003, and a continuation-in-part of U.S. application Ser. No. 10/153,622, filed on May 24, 2002, which is a continuation-in-part of U.S. application Ser. No. 09/434,380, filed on Nov. 5, 1999, now U.S. Pat. No. 6,426,507, all of which are herein incorporated by reference.

BACKGROUND OF THE INVENTION

1. Field of the Invention

This invention relates to a particle beam processing apparatus and materials treatable using such apparatus. In particular, this invention relates to a particle beam processing apparatus including a particle generating assembly, a foil support assembly having a thin foil, and a processing zone. When the treatable material is exposed to the particles generated by the apparatus, the particles cause a chemical reaction on a coating of the material.

2. Description of the Related Art

A particle beam processing device is commonly used to expose a substrate or coating to highly accelerated particle beams, such as an electron beam (EB), to cause a chemical reaction on the substrate or coating.

An electron is a negatively charged particle found in all matter. Electrons revolve around the nucleus of an atom much like planets revolve around the sun. By sharing electrons, two or more atoms bind together to form molecules. In EB processing, energetic electrons are used to modify the molecular structure of a wide variety of products and materials. For example, electrons can be used to alter specially designed liquid coatings, inks and adhesives. During EB processing, electrons break bonds and form charged particles and free radicals. These radicals then combine to form large molecules. By this process, the liquid is transformed into a solid. This process is known as polymerization.

Liquid coatings treated with EB processing may include printing inks, varnishes, silicone release coatings, primer coatings, pressure sensitive adhesives, barrier layers and laminating adhesives. EB processing may also be used to alter and enhance the physical characteristics of solid materials such as paper, substrates and non-woven textile substrates, all specially designed to react to EB treatment.

A particle beam processing device generally includes three zones, i.e., a vacuum chamber zone where a particle beam is generated, a particle accelerator zone, and a processing zone. In the vacuum chamber, a tungsten filament is heated to about 2400K, which is the thermionic emission temperature of tungsten, to create a cloud of electrons. A positive voltage differential is then applied to the vacuum chamber to extract and simultaneously accelerate these electrons. Thereafter, the electrons pass through a thin foil and enter the processing zone. The thin foil functions as a barrier between the vacuum chamber and the processing zone. Accelerated electrons exit the vacuum chamber through the thin foil and enter the processing zone at atmospheric conditions.

Electron beam processing devices that are commercially available at the present time generally operate at a minimum voltage of 125 kVolts. These existing EB units utilize thin foil made of titanium having a thickness of 12.5 micrometers, to cure coatings on substrates that are being fed through the processing devices at a rate of 800–1000 feet per minute. Such an EB unit may be purchased from Energy Sciences, Inc. of Wilmington, Mass., Model No. 125/105/1200. The current technology cannot be used in certain industries, e.g., flexible food packaging. An EB unit operating at 125 kVolts deposits substantial amounts of the energy onto the polyethylene based sealant films which contact the food being packaged. This deposit causes off-odors in the films and increases its seal initiation temperatures.

The efficiency of such EB units can be improved by reducing the operating voltage below 125 kVolts. In addition, operating below 125 kVolts allows better control of the depth of energy deposition and minimizes the electron energy absorbed by the sealant films. However, when the voltage is reduced below 125 kVolts, the kinetic energy of the electrons traveling through the titanium foil decreases because more energy is being absorbed by the titanium foil, causing the foil to heat up excessively. Excessive heat causes the titanium foil to become blue, brittle, and lose its mechanical strength. Excessive heat also poses a problem with heat management of the system. Consequently, the feed rate of the substrate must be substantially reduced which makes the processing device commercially unviable.

In light of the foregoing, there is a need for a particle beam processing device that operates more efficiently, is smaller in size, has a reduced power demand, and is cheaper to construct.

SUMMARY OF THE INVENTION

Methods, and materials made by the methods, are provided herein for treating materials with a particle beam processing device. According to one illustrative embodiment, a method for treating a material with a particle beam processing device is provided that includes: providing a particle beam generating assembly including at least one filament for creating a plurality of particles; applying an operating voltage greater than about 110 kV to the filament to create the plurality of particles; causing the plurality of particles to pass through a thin foil having a thickness of about 10 microns or less; and treating a material with the plurality of particles.

According to another illustrative embodiment, a multi-layered material is provided that includes a first material layer, a second EB cured adhesive layer, a third material layer, a fourth EB cured adhesive layer, and a fifth material layer.

According to another illustrative embodiment, a method for treating a material with a plurality of particles emanating from a particle beam processing device is provided that includes: selecting a foil thickness through which the plurality of particles passes, and selecting an operating voltage, wherein the foil thickness and the operating voltage are selected to achieve at least about 80% surface dose at a depth of at least about 20 grams/$m^2$.

It is to be understood that both the foregoing general description and the following detailed description are exemplary and explanatory only and are not restrictive of the invention as claimed. Additional advantages will be set forth in the description that follows, and in part will be understood from the description, or may be learned by practice of the invention. The advantages and purposes may be obtained by means of the combinations set forth in the attached claims.

BRIEF DESCRIPTION OF THE DRAWINGS

The accompanying drawings, which are incorporated in and constitute a part of this specification, illustrate several embodiments of the invention and, together with the description, serve to explain the principles of the invention. In the drawings.

DETAILED DESCRIPTION OF THE EMBODIMENTS

Reference will now be made in detail to several embodiments of apparatus, materials, and methods consistent with the invention, examples of which are illustrated in the accompanying drawings. Wherever possible, the same reference numbers will be used throughout the drawings to refer to the same or like parts. Moreover, the invention will be further clarified by the examples which follow.

A particle beam processing device according to one illustrative embodiment of the present invention can be made relatively small in size and to operate at high efficiency due to at least two features: (1) the operating voltage is reduced to 110 kVolts or less, and (2) the thin foil, if made of titanium or alloys thereof, has a thickness of 10 micrometers or less, and if made of aluminum or alloys thereof, has a thickness of 20 micrometers or less.

In accordance with the principles of the present invention, a particle beam processing device comprises a power supply, a particle generating assembly, a foil support assembly, and a processing assembly.

Figure 1:
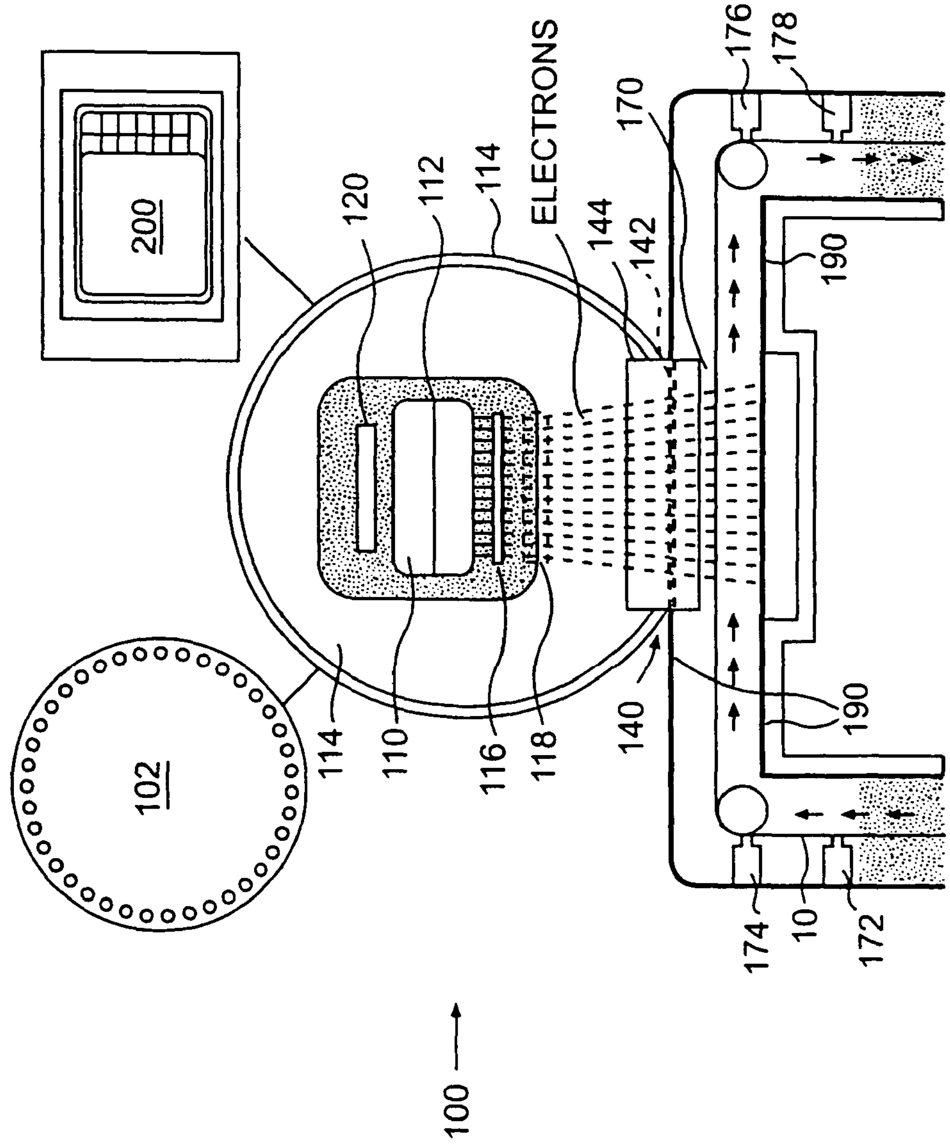
FIG. 1 is a schematic view of the particle beam processing device according to one embodiment of the present invention.

FIG. 1 schematically illustrates a particle beam processing device 100 consistent with the principles of one illustrative embodiment of the invention, including power supply 102, particle beam generating assembly 110, foil support assembly 140, and processing assembly 170. Power supply 102 preferably provides an operating voltage of 110 kVolts or less, more preferably in a range of 90–100 kVolts, to the processing device 100. Power supply 102 may be of a commercially available type that includes multiple electrical transformers located in an electrically insulated steel chamber to provide high voltage to particle beam generating assembly 110 to produce particles, such as electrons.

Particle beam generating assembly 110 is preferably kept in a vacuum environment of vessel or chamber 114. In an EB processing device, particle generating assembly 110 is commonly referred to as an electron gun assembly. Evacuated chamber 114 may be constructed of a tightly sealed vessel in which particles, such as electrons, are generated. Vacuum pump 212 (shown in FIG. 3) is provided to create a vacuum environment in the order of approximately $10^{-6}$ Torr. Inside the vacuum environment of chamber 114, a cloud of electrons are generated around filament 112 when high-voltage power supply 102 sends electrical power to heat up filament 112.

Filament 112 then glows white hot and generates a cloud of electrons. Electrons are then drawn from filament 112 to areas of higher voltage, since electrons are negatively charged particles, as described below and accelerated to extremely high speeds. Filament 112 may be constructed of one or more wires commonly made of tungsten, and may be configured to be spaced evenly across the length of foil support 144 and emits electron beams across the width of a substrate 10.

Figure 2:
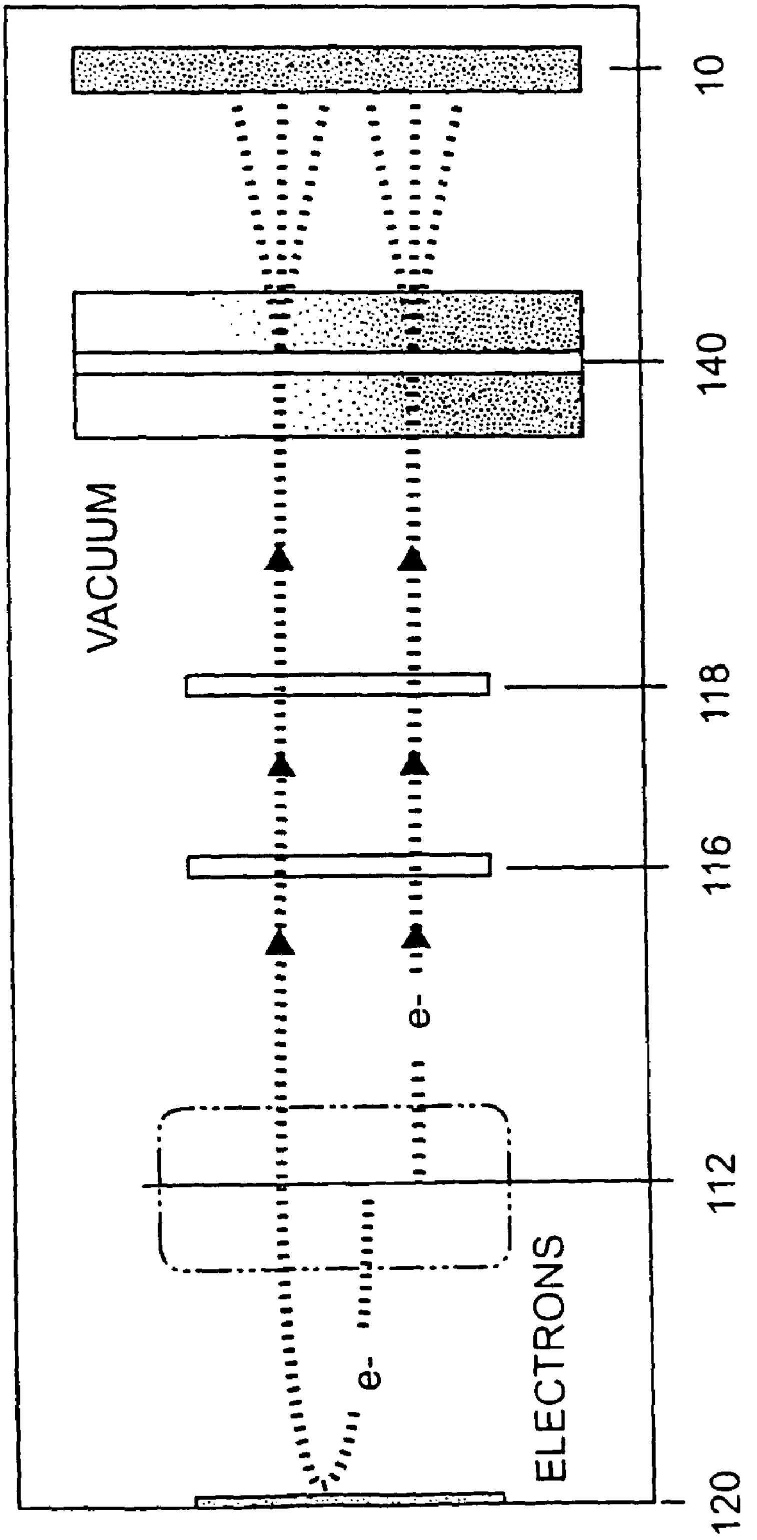
FIG. 2 is a schematic view of a voltage profile of an electron beam.

As shown in FIGS. 1 and 2, particle beam generating assembly 110 may include an extractor grid 116, a terminal grid 118, and a repeller plate 120. Repeller plate 120 repels electrons and sends the electrons toward extractor grid 116. Repeller plate 120 operates at a different voltage, preferably slightly lower, than filament 112 to collect electrons escaping from filament 112 away from electron beam direction as shown in FIG. 2.

Extractor grid 116, operating at a slightly different voltage, preferably higher than filament 112, attracts electrons away from filament 112 and guides them toward terminal grid 118. Extractor grid 116 controls the quantity of electrons being drawn from the cloud, which determines the intensity of the electron beam.

Terminal grid 118, operating generally at the same voltage as extractor grid 116, acts as the final gateway for electrons before they accelerate to extremely high speeds for passage through foil support assembly 140.

According to one embodiment of the present invention, for example, filament 112 may operate at −110,000 Volts and foil support assembly 140 may be grounded or set at 0 Volt. Repeller plate 120 may be selected to operate at −110,010 Volts to repell any electrons towards filament 112. Extractor grid 116 and terminal grid 118 may be selected to operate in a range of −110,000 Volts to −109,700 Volts.

The electrons then exit vacuum chamber 114 and enter the foil support assembly 140 through a thin foil 142 to penetrate a coated material or substrate 10 for the chemical reaction. The chemical reaction includes, for example, polymerization, crosslinking or sterilization. The speed of the electrons may be as high as or above 100,000 miles per second. Foil support assembly 140 may be made up of a series of parallel copper ribs (not shown). Thin foil 142, as shown in FIG. 1, is securely clamped to the outside of foil support assembly 144 to provide a leak-proof vacuum seal inside chamber 114. High speed electrons pass freely between the copper ribs, through thin foil 142 and into substrate 10 being treated. To prevent an undue energy loss, the foil is preferably made as thin as possible while at the same time providing sufficient mechanical strength to withstand the pressure differential between the vacuum state inside particle generating assembly 110 and processing assembly 170.

In accordance with the principles of this illustrative embodiment of the present invention, the particle beam generating device can be made smaller in size and operate at a higher efficiency level when the thin foil of the foil support assembly is made of titanium or alloys thereof and having a thickness of 10 micrometers or less, preferably in a range of 3–10 micrometers, more preferably in a range of 5–8 micrometers. Alternatively, thin foil 142 may also be constructed of aluminum or alloys thereof having a thickness of 20 micrometers or less, preferably in a range of 6–20 micrometers, more preferably in a range of 10–16 mircometers.

Figure 3:
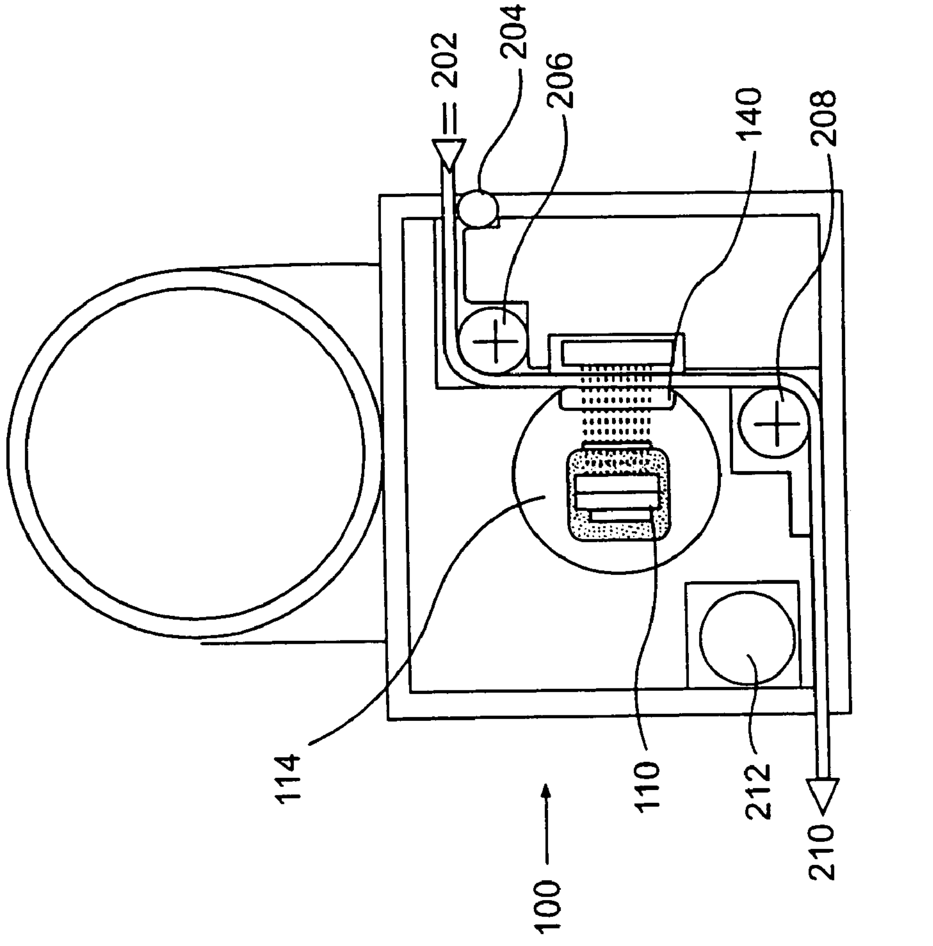
FIG. 3 is a front view of the particle beam processing device according to the preferred embodiment of the present invention.

Once the electrons exit the foil support assembly 140, they enter the processing assembly 170 where the electrons penetrate a coating or web substrate 10 and cause a chemical reaction resulting in polymerization, crosslinking or sterilization. As shown in FIG. 3, the coating or web substrate 10 is being fed into the processing device 100 to enter processing assembly 170. Processing assembly 170 includes a web entrance 202 where substrate 10 enters, rollers 204, 206, and 208 to guide and deliver substrate 10 through the processing assembly 170, and a web exit 210 where substrate 10 exits the processing device 100. The product being treated is instantaneously transformed, needs no drying or cooling and contains many new and desirable physical properties. Products can be shipped immediately after processing.

The particle beam processing device may include a protective lining surrounding at least a portion of the periphery of the device to absorb radiation, such as X-ray, emitted when the electrons decelerate as they are absorbed in matter.

As shown in FIG. 1, a protective lining 190 surrounds the periphery of processing device 100, such as evacuated chamber 114 and processing assembly 170. Protective lining 190 absorbs substantially all X-rays created when electrons decelerate in matter. The thickness and material selected for protective lining 190 form a function primarily determined by the desired absorption rate of the X-rays. In one embodiment, protective lining 190 is preferably capable of absorbing X-ray radiation at an absorption rate with residuals less than or equal to approximately 0.1 mrem/hour. The unit mrem/hour represents an absorption of 0.1 mili radiation equivalent to man per one hour. One milirem is equivalent to 1 milirad for electrons and X-rays. One way to measure the radiation emitted is by measuring the absorption at a distance of 10 cm away from protective lining 190 by an instrument such as an ionization chamber instrument commercially known as Bicron RSO-5. To further enhance safety measure of particle beam processing device 100, a safety interlock switches (not shown) may be provided to ensure safe operation by automatically stopping production whenever interlocks are opened.

The particle beam processing device may further include a processor, such as a computerized microprocessor, to regulate the quantity of electrons generated so the electron beam output is proportional to the feeding speed of the substrate. As shown in FIG. 1, a process control system 200 is provided to control several processes including but not limited to maintaining the required vacuum environment, initiating system operation with predetermined voltages and filament power, synchronizing electron generation with process speed to maintain constant treatment level, monitoring functions and interlocks, and providing warnings and/or alarms whenever the system functions exceed set limits or an interlock problem is detected.

In operation, particle beam processing device 100 works as follows. A vacuum pump 212 (shown in FIG. 3) evacuates air from chamber 114 to achieve a vacuum level of approximately $10^{-6}$ Torr, at which point processing device 100 is fully operational. In particle generating assembly 110, particle gun assembly components, including repeller plate 120, extractor grid 116, and terminal grid 118, are set at three independently controlled voltages which initiate the emission of electrons and guide their passage through foil support 144.

During the particle beam processing, a combination of electric fields inside evacuated chamber 114 create a "push/pull" effect that guides and accelerates the electrons toward thin foil 142 of foil support 144, which is at ground (0) potential. The quantity of electrons generated is directly related to the voltage of extractor grid 116. At slow production speeds, extractor grid 116 is set at a lower voltage than at high speeds, when greater voltage is applied. As the voltage of extractor grid 116 increases, so does the quantity of electrons being drawn from filament 112.

The coatings to be cured, for example, inks, adhesives and other coatings, generally require a low oxygen environment to cause the chemical conversion from a liquid state into a solid state. Therefore, the particle beam processing device according to this embodiment may include, as illustrated in FIG. 1, a plurality of nozzles 172, 174, 176, and 178 distributed in processing zone 170 to inject gas other than oxygen to displace the oxygen therein. In one embodiment, nitrogen gas is selected to be pumped into processing zone 170 through nozzles 172, 174, 176, and 178 to displace the oxygen that would prevent complete curing.

As can be seen from the description above, particle beam processing device 100 can be calibrated to achieve extremely high precision specification because process control system 200 may be set to provide the exact depth level of cure desired on a substrate or coating. Process control system 200 calculates the dose and the depth of electron penetration into the coating or substrate. The higher the voltage, the greater the electron speed and resultant penetration.

Dose is the energy absorbed per unit mass and is measured in terms of megarads (Mrad), which is equivalent to 2.4 calories per gram. A higher number of electrons absorbed reflects a higher dose value. In application, dose is commonly determined by the material of the coating and the depth of substrate to be cured. For example, a dose of 5 Mrad may be required to cure a coating on a substrate that is made of rice paper and having a mass density of 20 gram/m$^2$. Dose is directly proportional to the operating beam current which is the number of electrons extracted, and inversely proportional to the feed speed of the substrate, as expressed by the following formula:

$$\text{Dose}=K\cdot(I/S)$$

whereby I is the current measured in mAmp, S is the feed speed of the substrate measured in feet/min, and K is a proportionality constant which represents a machine yield of the processing device, or the output efficiency of that particular processing device.

Figure 4:
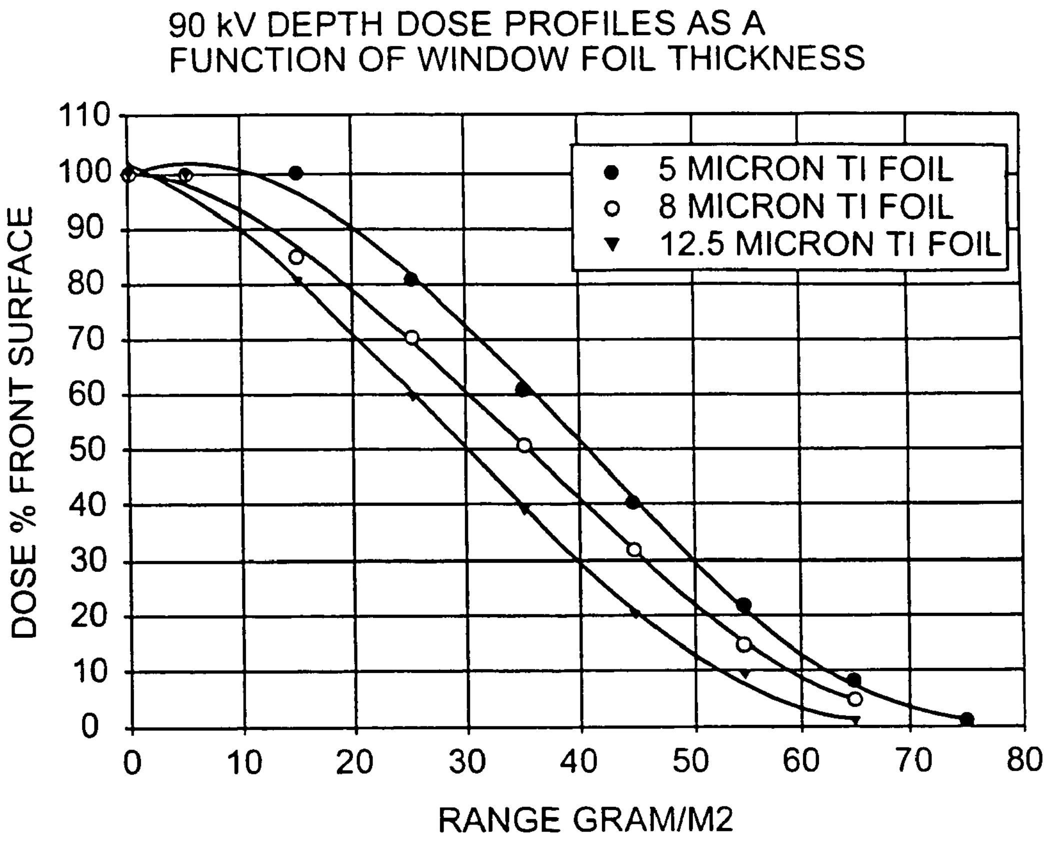
FIG. 4 is a chart of depth dose profiles as a function of thickness of titanium foil measured at an operating voltage of 90 kVolts.
Figure 5:
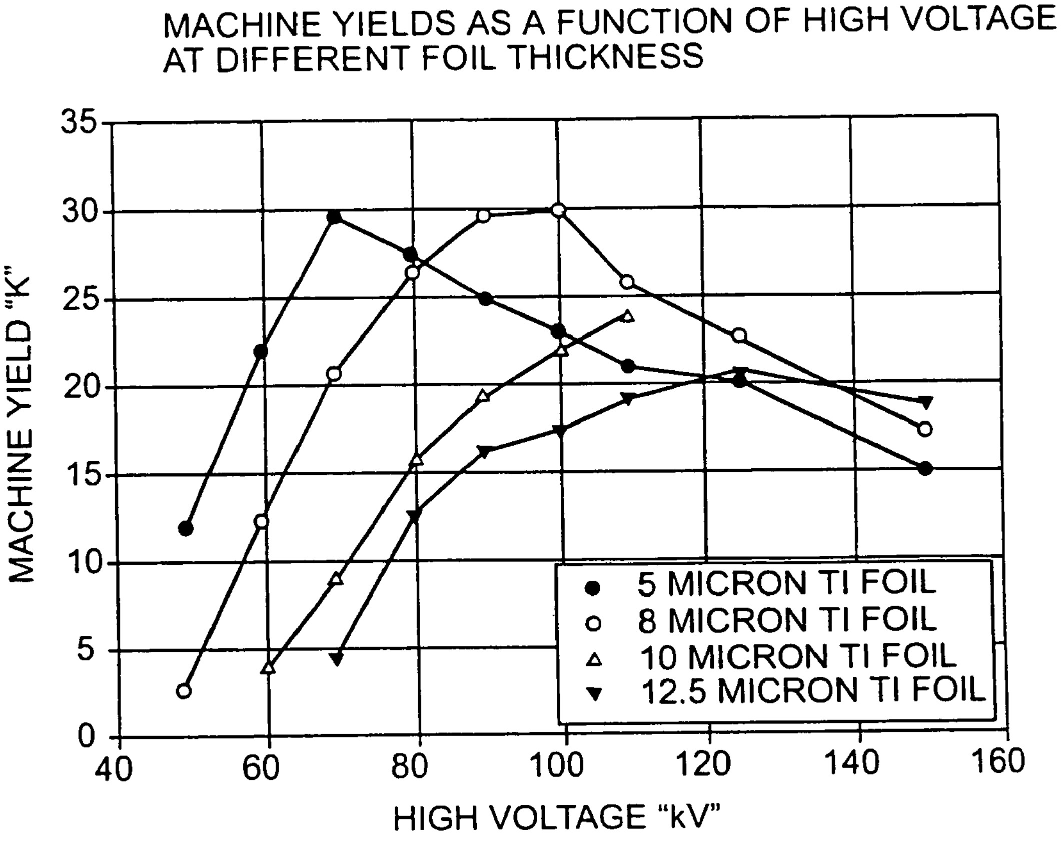
FIG. 5 is a chart of machine yields for a processing device having a width of 1.5 feet as a function of operating voltage measured using titanium foil thicknesses of 5, 8, 10 and 12.5 micrometers.
Figure 6:
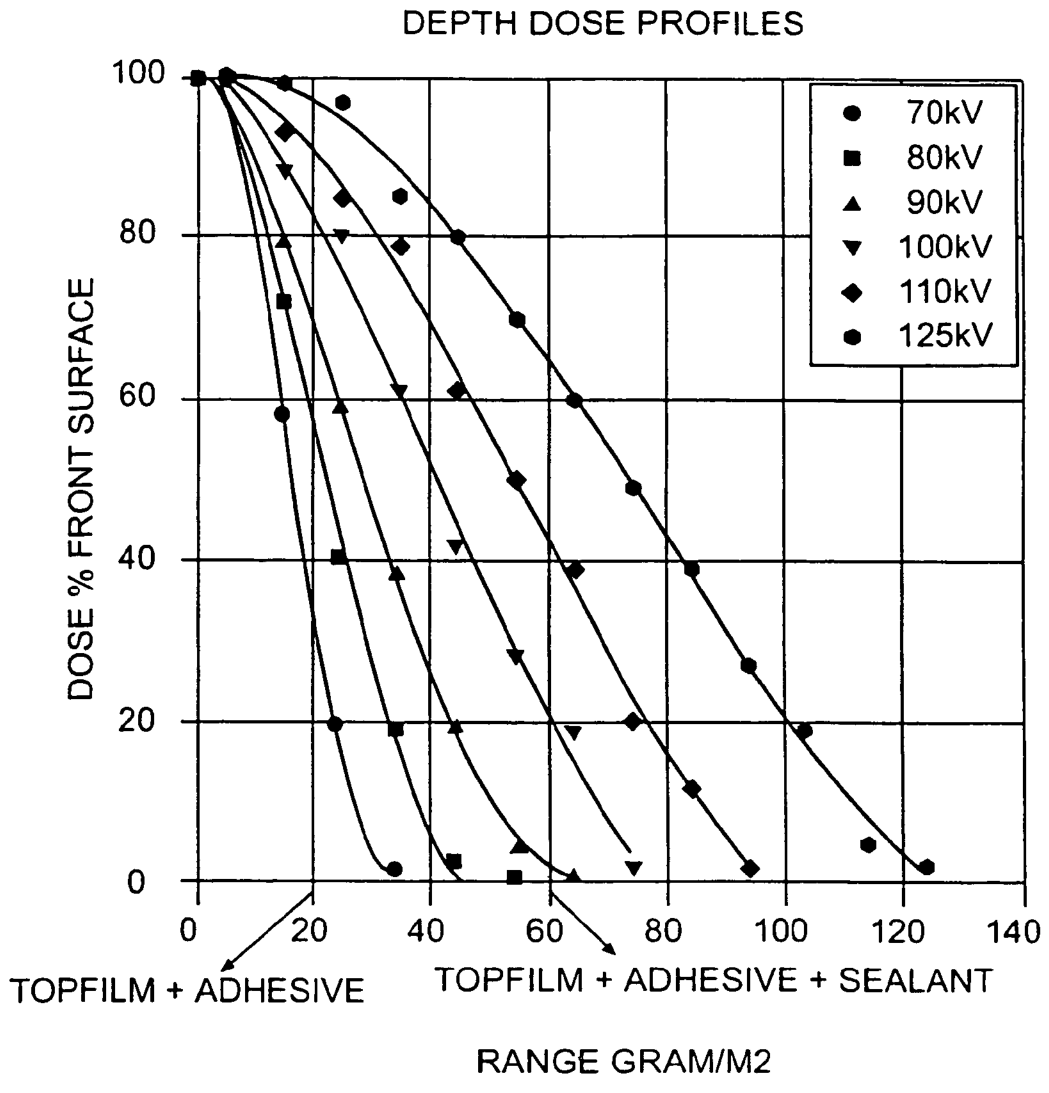
FIG. 6 is a chart of depth dose profiles as a function of thickness of titanium foil measured at various operating voltages.
Figure 7:
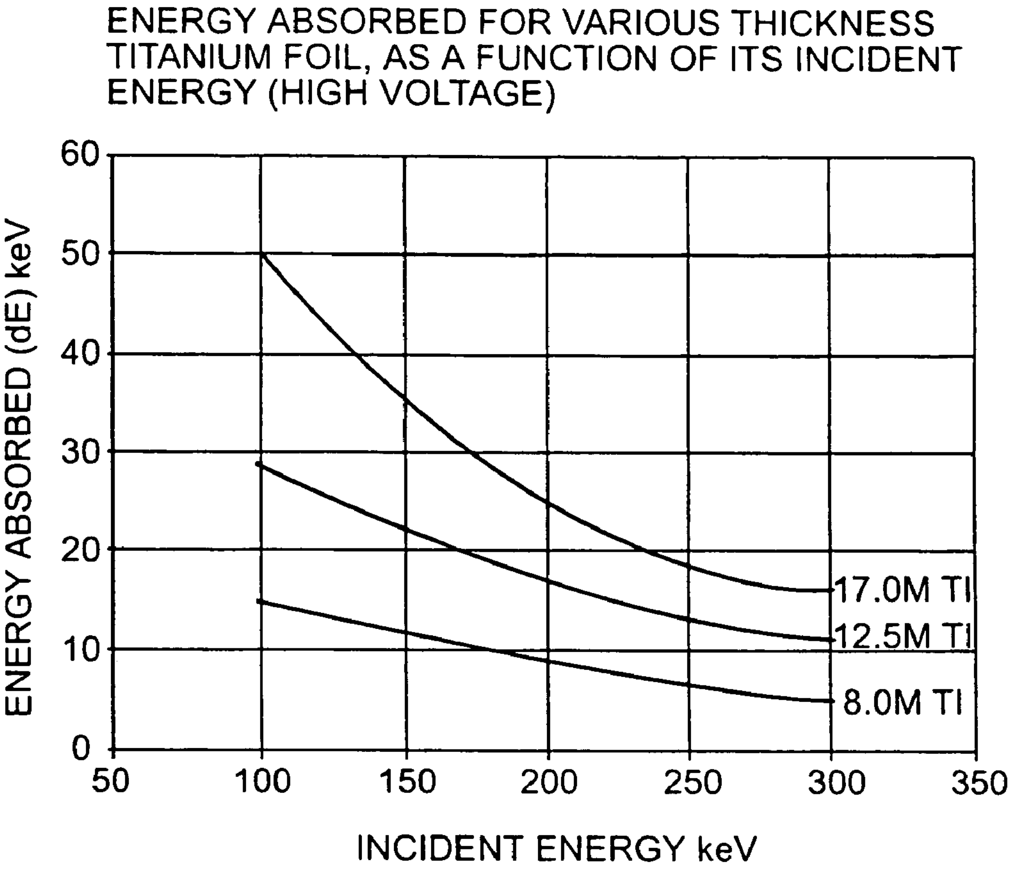
FIG. 7 is a chart of energy absorbed by the thin foil as a function of the incident energy in keV measured using titanium foil thicknesses of 17, 12.5, and 8 micrometers.

The following examples as illustrated in the charts shown in FIGS. 4–7 are provided as a result of a series of experiments. FIG. 4 illustrates the relationship between depth dose profiles and mass density of the coatings with respect to three different thicknesses of the thin foil as measured at an operating voltage of 90 kV. FIG. 5 illustrates the relationship between operating voltage ("High Voltage") as measured in kVolts and the machine yield K for a processing device having a width of 1.5 feet with respect to thin foil made of titanium having thicknesses of 5, 8, and 12.5 micrometers. FIG. 6 illustrates the relationship between depth dose profiles and mass density of the coatings with respect to various operating voltages. FIG. 7 illustrates the relationship between energy absorbed by the thin foil ("dE") measured in keV and incident energy or operating voltage measured in keV with respect to three titanium foil having thickness of 17, 12.5, and 8 micrometers.

The goal of this embodiment of the present invention is to increase the output efficiency of the processing device by applying an operating voltage that is as low as possible to reduce the power needed to generate the operating voltage which makes the processing device more compact and cheaper to build. Thus, as shown in the depth dose profiles of FIG. 6, the optimum curve preferably moves closer towards an imaginary vertical line crossing the X-axis representing the density of the coating to be cured. However, as previously discussed, reducing the operating voltage causes a tremendous heat problem which renders the processing device not commercially viable. As illustrated in FIGS. 4 and 7, heat problem can be solved by utilizing a titanium foil that has a thickness of 10 micrometers or less.

The data taken in these experiments was measured utilizing thin film dosimetry techniques. Dosimetry techniques involve nylon films which have thicknesses in the range of 9–10 micrometers. The dosimeters contain a radiochromic dye that changes color from colorless to blue when the dye is exposed to electromagnetic radiation. The intensity of the blue color is directly proportional to the amount of radiation exposure obtained from the nylon films. By measuring the intensity or optical density of the blue color using a densitometer, one can convert the measured optical density to the absorbed dose in Mrads. The conversion from optical density to dose in Mrads is achieved by prior calibration of the dosimeters and the densitometer using $Co^{6o}$ Gamma facility at the National Institute of Standards and Technology, Gaithersburg, Md. These experiments utilized Dosimeters Model FWT-60-810 manufactured by Far West Technology, Goleta, Calif. and Densitometer Model 92 SXN 3285 manufactured by Far West Technology, Goleta, Calif.

EXAMPLE 1

The result of a first experiment, shown in FIG. 4, indicates that particle beam processing device 100 using thin foil 142 that is made of titanium having a thickness of less than 12.5 micrometer improves the electron penetration in substrate 10.

In the first experiment, thin film nylon dosimeters were used to measure the penetration capability of electrons. The parameters for this experiment include: a constant operating voltage of 90 kVolts, a dose of 5 Mrads, and a thin titanium foil. Three specimens were tested to study three different titanium foil thicknesses of 12.5, 8, and 5 micrometers, one for each foil thickness.

The three specimens were made of thirty dosimeters, each having a surface area of approximately 2×2 $cm^2$. These dosimeters were divided into three stacks, each stack containing an arrangement of ten dosimeters one on top of the other. One edge of each stack of dosimeters was taped to a polyester carrier having a thickness of 125 micrometer. The three polyester carriers were then taped to a paper substrate and fed through processing device 100 to receive radiation treatment. The first stack was treated in processing device 100 with 12.5 micrometer titanium foil; the second stack with 8 micrometers, and the third stack with 5 micrometers. Following the radiation treatment, the three stacks were annealed in an oven at 60° C. for 5 minutes. The dosimeters were then separated, individually measured on the densitometer, and converted to dose in terms of Mrads. For each stack, the dose values obtained were normalized to the first dosimeter.

FIG. 4 shows the data resulted from this experiment with the Y-axis representing the normalized dose for each stack and the X-axis representing the mass density in terms of gram/$m^2$. The mass density was obtained by measuring the dosimeters mass density that resulted in 10 grams/$M^2$. It is assumed that the first point is at one half of the mass density, and then each mass density is added to it for subsequent points. This experiment concludes that the thinner the foil is used in particle beam processing device 100, the higher electron penetration on substrate 10 is achieved.

EXAMPLE 2

The result of a second experiment, shown in FIG. 5, indicates that thinner foil not only improves electron penetration on a substrate, but also increases the efficiency or machine yield K.

In the second experiment, similar to the first experiment, thin film nylon dosimeters were used to measure the machine yield K of a processing device having a width of 1.5 feet at various operating voltages measured in kVolts. Four measurements were run to study four different titanium foils having thicknesses of 12.5, 10, 8, and 5 micrometers.

The value of machine yield K was obtained by calculating the average of nine individual dosimeter chips. Each dosimeter of 2×2 $cm^2$ was taped on one edge to a polyester carrier. Each polyester carrier contained nine dosimeters. The polyester carrier was taped to the paper substrate and fed through processing device 100 to receive radiation treatment. After irradiation the dosimeters were annealed at 60° C. for 5 minutes. Thereafter, the optical density and the dose value were measured. For each measurement, processing device 100 was set to deliver 4 Mrads to the dosimeters. Processing device 100 included several gauges (not shown) to indicate the feed rate of the substrate in feet/minute and the current of the particle beam in mAmp. The average dose was determined and used to calculate the K value according to the following equation:

$$K(Mrads\text{-feet/min}/mAmp) = \frac{\text{Dose }(Mrads) \times \text{Speed (feet/min)}}{\text{Current }(mAmp)}$$

The same procedure was repeated for all voltages.

FIG. 5 shows the data resulted from this experiment with the Y-axis representing the machine yield K and the X-axis representing the operating voltages in kVolts. This experiment concludes that thinner foil increases the efficiency or machine yield K. Machine yield K of the processing device in accordance with this embodiment increases, and reaches an optimum value at the corresponding optimum operating voltage. As shown in FIG. 5, when a 10 micrometer titanium foil is used and the processing device operates at 110 kVolts, the machine yield reaches approximately 23. When an 8 micrometer titanium foil is used and the processing device operates at 100 kVolts, the machine yield reaches approximately 30 at 90–100 kVolts. Similarly, when a 5 micrometer titanium foil is used and the processing device operates at 70 kVolts, the machine yield reaches almost 30. Comparing the machine yield K between the processing device using 12.5 micrometer titanium foil and the processing devices using 10, 8 and 5 micrometers titanium foils, the following relationship is deduced:

$$K \geqq 20/L$$

for a 10 micrometer titanium foil operating at a voltage of 80–110 kvolts;

for an 8 micrometer titanium foil operating at a voltage of 70–110 kvolts;

for a 5 micrometer titanium foil operating at a voltage of 60–110 kVolts;

wherein L is the width of the processing device measured in feet, in this case 1.5 feet.

EXAMPLE 3

The result of a third experiment, as shown in FIG. 6, illustrates one advantage of operating processing device 100 at a voltage of 110 kVolts or less in the field of Flexible Food Packaging.

In the third experiment, depth dose profiles for processing device 100 at various operating voltages were measured according to the procedure described earlier with respect to the first experiment. A typical application of flexible food packaging is the packaging for processed meat and cheese which commonly include three layers top film, adhesive, and sealant. For example, Table 1 below provides a typical packaging layers and their normalized thicknesses, measured in grams/m$^2$:

TABLE 1

| | |
|---|---|
| Top film of 0.5 mil polyester type (PET): | 17.0 gram/m$^2$ |
| Adhesive: | 3.0 gram/m$^2$ |
| Sealant of polyethylene copolymer: | 40.0 gram/m$^2$ |

Electron beam has generally been used to cure the adhesive in between the top film and the sealant.

As illustrated in FIG. 6, EB processing device currently available in the market, which operates at 125 kVolts, sufficiently cured the adhesive at a depth of 20 gram/m$^2$, curing the top film and the adhesive. However, it deposited significant dose to the sealant layer at a depth of 60 gram/m$^2$ (top film, adhesive, and sealant). The polyethylene based sealant layer, which contacts the food being packaged, emits undesirable odors when it absorbs the dose deposited thereon. In addition, the deposited dose also increases the seal initiation temperatures, thus making it difficult to heat seal. These two effects on the sealant layer prevent the current EB processing device from meeting the demands for flexible food packaging industry.

Processing device 100 consistent with the principles of this embodiment of the present invention overcomes the problems of prior processing device by operating at a voltage range of 110 kVolts or less, preferably 90–100 kVolts, at a commercially viable substrate feed rate. As shown in FIG. 6, at the operating voltage of 110 kVolts or less, one can properly cure the adhesive at a depth of 20 gram/m$^2$, yet impart significantly less dose, and thus cause less damage to the sealant film.

EXAMPLE 4

The result of a fourth experiment, as shown in FIG. 7, describes the relation between the energy absorbed by the titanium foil as a function of its operating voltage measured in kVolts. This study compared three different titanium foil thicknesses of 17, 12.5, and 8 micrometers. The studies on the 17 and 12.5 micrometers were performed at the National Institute of Standards and Technology according to the electron energy dissipation in titanium foil using Monte-Carlo calculations. Based on the data resulted from these studies, data for the 8 micrometer titanium foil was extrapolated. This study confirms that thinner foil absorbs less energy, especially at lower voltages. Therefore, a processing device utilizing foil having a thickness of 10 micrometers or less solves the heat management problem since energy absorbed by the foil converts to power resulting in heat management issues with the foil.

Because the processing device according to this embodiment can operate at an operating voltage of 110 kVolts or less, not only that the size of power supply to generate the operating voltage can be reduced, but also the size of evacuated vessel to contain the particle beam generating assembly can be substantially reduced. Furthermore, the thickness of protective lining can be reduced because less severe radiation is emitted by the electrons exiting the evacuated vessel at a slower rate when the operating voltage is 110 kVolts or less.

In application, a particle beam processing device may be used in a manufacturing process, such as electron beam (EB) processing, to treat a substrate or a coating exposed to the device. The treatment may include a chemical reaction, such as polymerization, crosslinking, or sterilization. When the substrate or coating is exposed to highly accelerated electrons, a reaction occurs in which the chemical bonds in the substrate or coating are broken and a new, modified molecular structure is formed. This application applies broadly to any particle beam, but for exemplary purposes, the electron beam is particularly described. The following will describe possible chemical reactions that could occur during EB processing.

EXAMPLE 5

Figure 8:
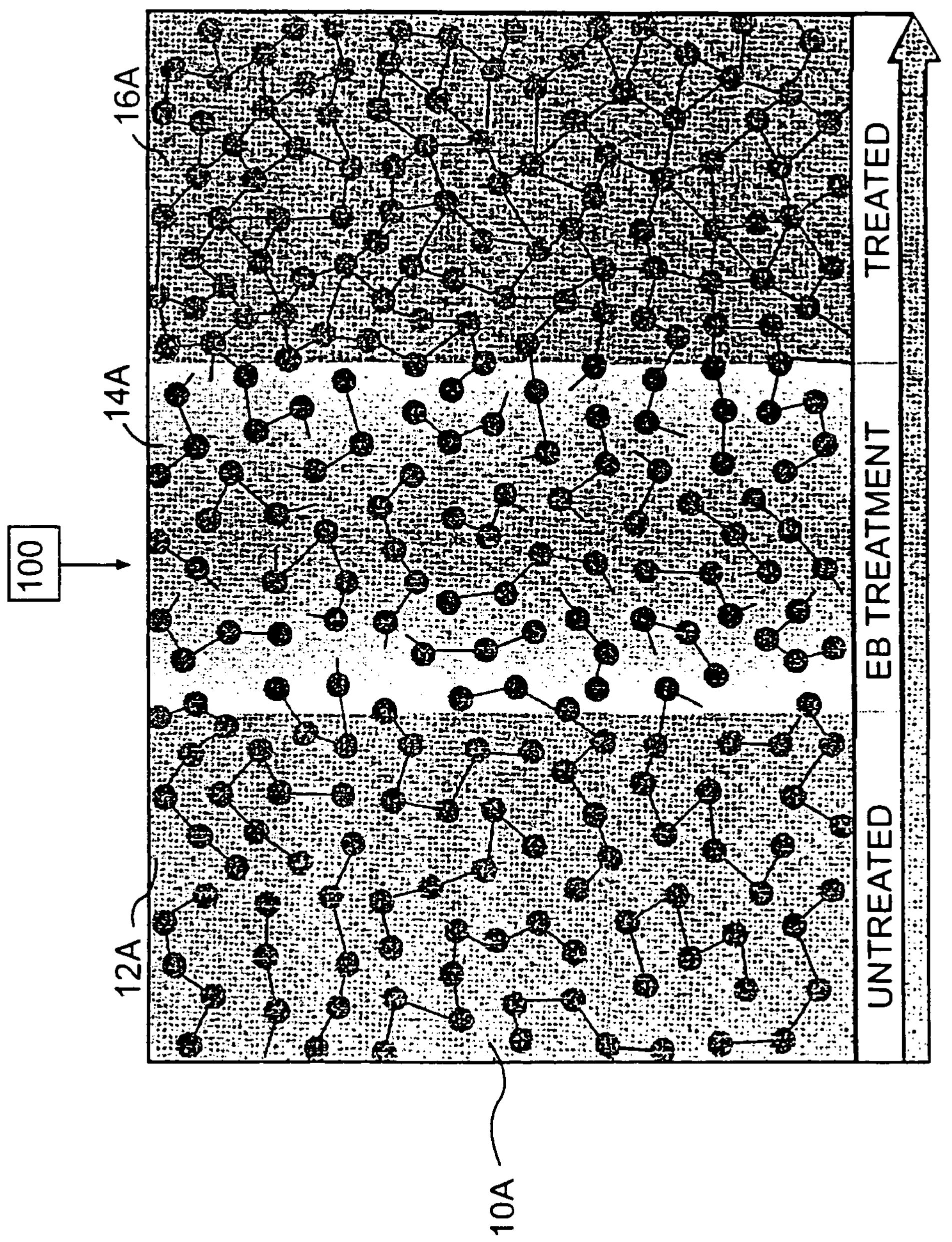
FIG. 8 is a schematic view of a crosslinking reaction on a substrate as the substrate passes through a particle beam processing device.

Crosslinking is a chemical reaction that alters and enhances the physical characteristics of the material being treated. In a crosslinking process, an interconnected network of chemical bonds or links develops between large polymer chains to form a stronger molecular structure. Application of EB processing by crosslinking reaction includes, for example, when a plastic like substrate or rubber substrate is treated with electrons, the large polymers in these products develop many linking bonds. These bonds increase the product's performance and its resistance to weakening at elevated temperatures. FIG. 8 illustrates the crosslinking reaction on substrate 10A as substrate 10A passes under the particle beam processing device, schematically referred to as 100, from an untreated state on the left area 12A, into an exposure area 14A, to a treated state on the right area 16A.

EXAMPLE 6

Figure 9:
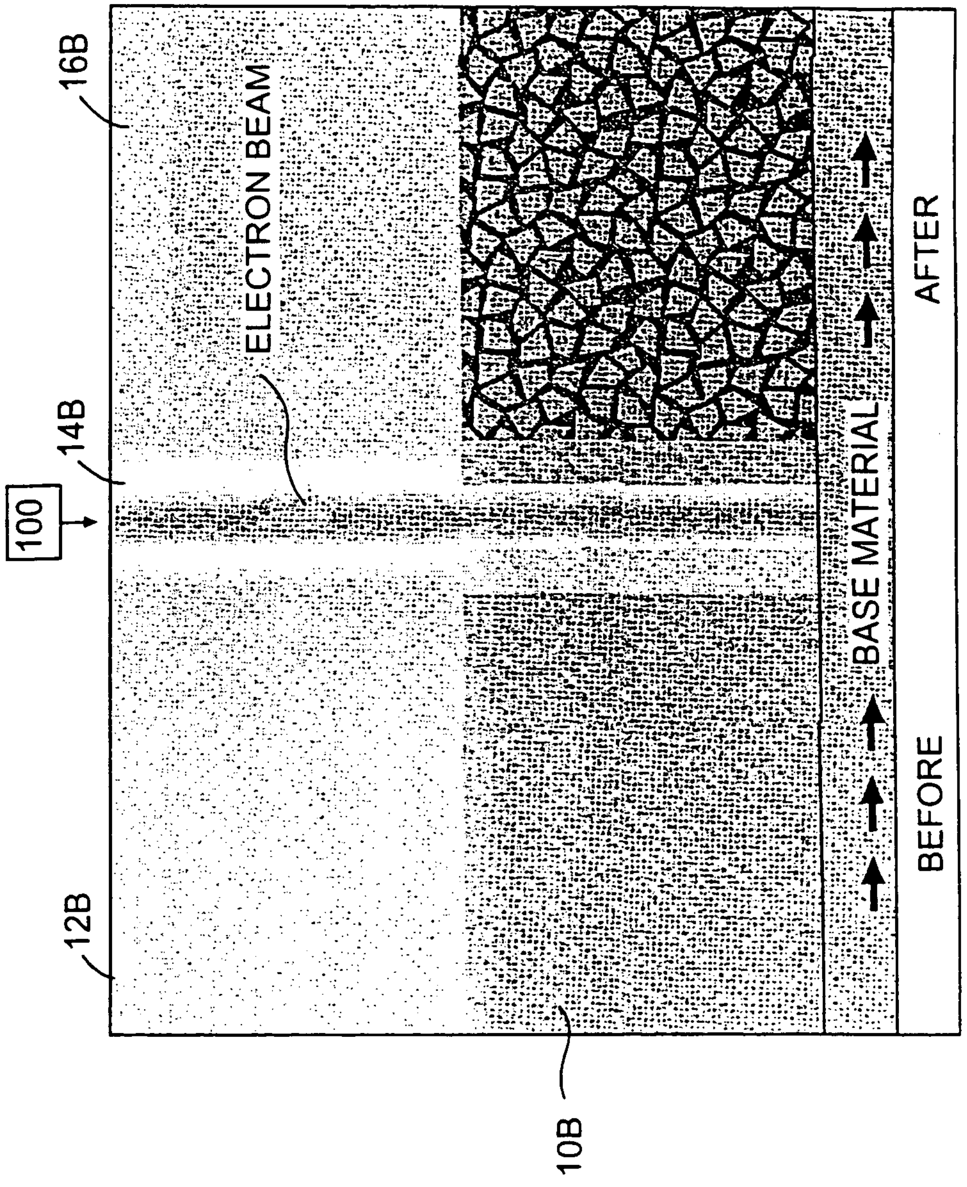
FIG. 9 is a schematic view of a polymerization reaction on a substrate as the substrate passes through the particle beam processing device.

Like crosslinking, polymerization is a process in which several individual groups of molecules combine together to form one large group called a polymer. This causes significant physical changes in the product being treated and results in many desirable physical characteristics such as high gloss and abrasion resistance. For example, when exposed to accelerated electrons during EB processing, furniture coatings and adhesives are transformed almost instantaneously from a liquid (uncured) state into a non-tacky (cured) solid state. FIG. 9 illustrates the polymerization reaction on substrate 10B as substrate 10B passes under particle beam processing device 100, from an untreated state on the left area 12B, into an exposure area 14B, to a treated state on the right area 16B.

EXAMPLE 7

Figure 10:
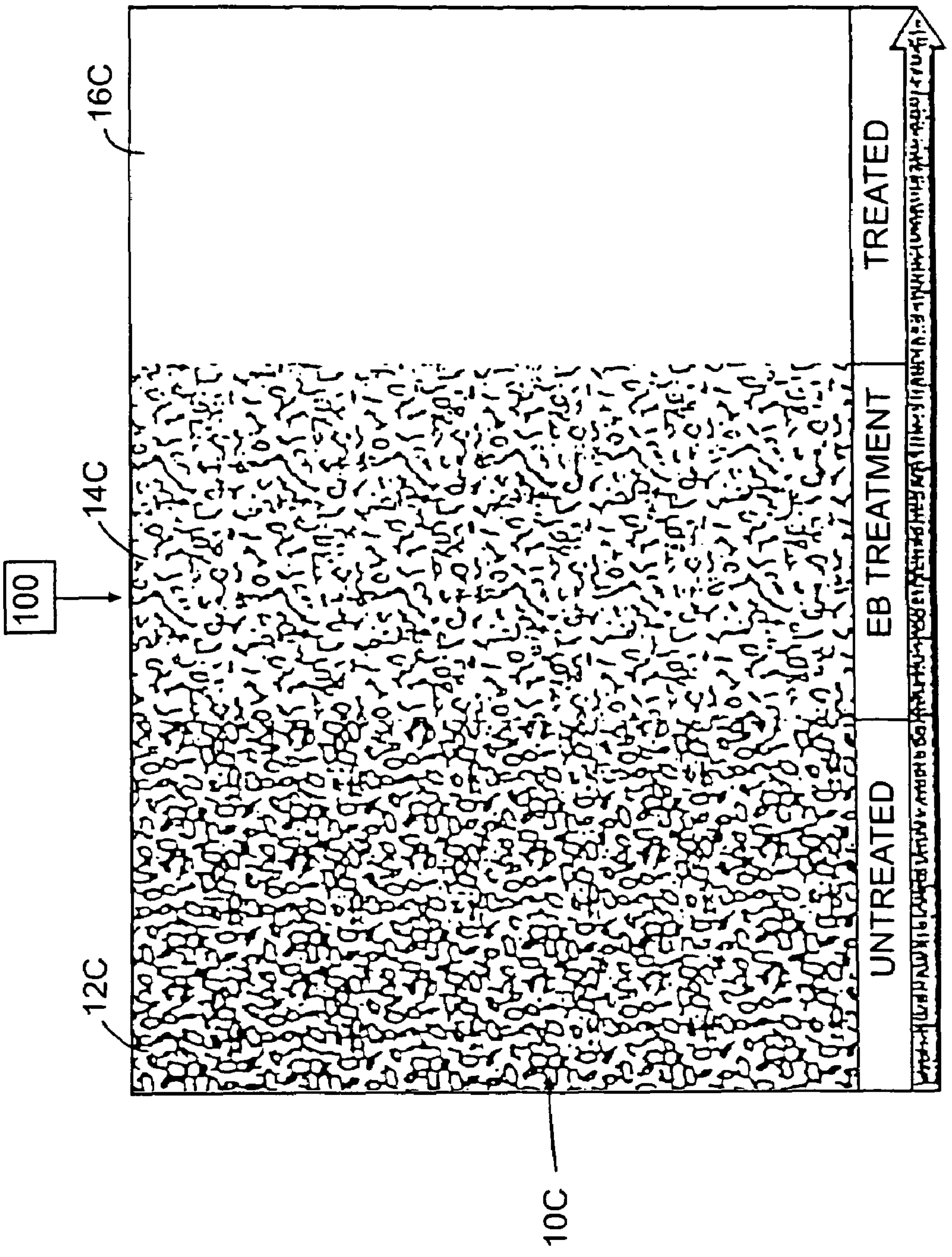
FIG. 10 is a schematic view of a sterilization reaction on a substrate as the substrate passes through the particle beam processing device.

Sterilization is a process of destroying contaminating microorganisms by rendering them sterile or unable to reproduce. EB sterilization occurs when electrons are directed into the microorganisms whereby breaking the DNA chains which control reproduction. Once a product has been sterilized, no microbial decomposition can take place. Since electrons act as a physical sterilizing agent rather than a chemical one, they do not change the chemistry of the target product or leave any residual chemicals. EB sterilization offers a number of advantages over chemical sterilization techniques, such as those that use hydrogen peroxide and ethylene oxide. For example, EB sterilization may be used to sterilize medical supplies and sensitive food products as well as their respective packaging, whereas chemical sterilization could not be used. FIG. 10 illustrates the sterilization reaction on substrate 10C as substrate 10C passes under particle beam processing device, schematically referred to as 100, from an untreated state on the left area 12C, into an exposure area 14C, to a treated state on the right area 16B.

In recent years, application of an EB processing has received wide acceptance in many different industries. For example, in the packaging industry, flexible packaging has experienced a tremendous successful growth compared to its counterpart rigid and semi-rigid packaging, such as cans and bottles packaging. One reason for this success over the rigid and semi-rigid packaging alternatives is that flexible packaging offers cost and source reduction. The particle beam processing device according to this embodiment, generally referred to in the industry as an EB machine, may be used to satisfy requirements of this industry, including to provide a flexible packaging material that is less expensive and meets the health and safety standards set forth by government agencies, such as the Food and Drug Administration. Cost reduction may be accomplished by using less raw material and employing an improved manufacturing technique. As an additional benefit, reducing the raw material also appreciably appeals to this industry as environmentally friendly.

As described above in Example 3 and exemplified in Table 1, a typical flexible packaging material currently available in the market comes in a laminate form, which means it has a minimum of two main layers: a top polymer film and a bottom polymer film, with an adhesive sandwiched or laminated between the top and bottom films. Each of the top and bottom films usually comes in the form of continuous sheet rolled around a cylindrical core or spool. The adhesive may be applied, for example, by squeezing it out of a nozzle into a nip area between a pair of rollers, one for guiding the top film, and another for the bottom film. Generally, also laminated and protected between the top and bottom films is a printing of the product label. The print is commonly a reversed image of the actual label itself.

Also currently known in the industry is an application of the particle beam processing device made according to the teaching of this application in the pet food packaging industry. For example, it is well known to use the EB machine of this illustrative embodiment to cure or polymerize a lacquer coating on the pet food packaging material such as multi-wall bag. Pet food packaging material is usually constructed of a layer of high strength paper and a lacquer coating to protect the label printed on the paper. It has been known to cure the lacquer coating on the paper by feeding the paper into a particle beam processing device of the present embodiment normally operating at a voltage of 110 kVolts to cure the lacquer coating, transforming the lacquer coating from a liquid phase to solid almost instantaneously. The lacquer coating is EB cured and designed to provide gloss, abrasion resistant and desired coefficient of friction (COF). After the EB lacquer is applied, the paper is further processed where other layers of paper and plastic film are glued onto the paper containing EB lacquer making the multi-wall bug substrate. After filling the contents, the paper packaging is then generally sealed by sewing the top and bottom edges of the packaging. The pet food packaging material does not include a bottom polymer film, which is normally made of polyethylene for heat sealing the packages when the EB lacquer is applied and cured with EB.

It is known that if the radiation from the particle beam processing device deposits significant dose to the bottom polymer film, thereby altering the sealing characteristics of the bottom polymer film, and causing the film to emit undesirable odors and raising the seal initiation temperatures thus making it difficult to heat seal the packages.

The present illustrative embodiment is directed to an application of the particle beam processing device to a treatable material, such as for a flexible food packaging, whereby the treatable material includes a substrate, a particle beam treatable lacquer coating, and a radiation labile layer, such as a sealing layer, whereby the particle beam causes the lacquer coating to chemically react without effecting the radiation labile layer.

Application of the particle beam processing device made according to this embodiment can be found in many industries including, for example, packaging, insulation films, reflective coatings and reflective materials, solar films, etc. Other fields, such as outer space suits and aircrafts, may also find this embodiment useful. For exemplary purposes, an embodiment of the present invention is discussed with respect to an application of the particle beam processing device in the flexible food packaging field.

Consistent with the principles of one illustrative embodiment of the present invention, in order to reduce material resources and production costs of current packaging material, this application provides a particle beam treatable material including a substrate and a lacquer coating applied on the substrate, the lacquer coating being formulated for exposure to highly accelerated particles, such as those generated by the particle beam processing device of this embodiment, to cause a chemical reaction to the lacquer coating. The particle beam processing device operates at a voltage in a range of 110 kVolts or below.

Figure 11:
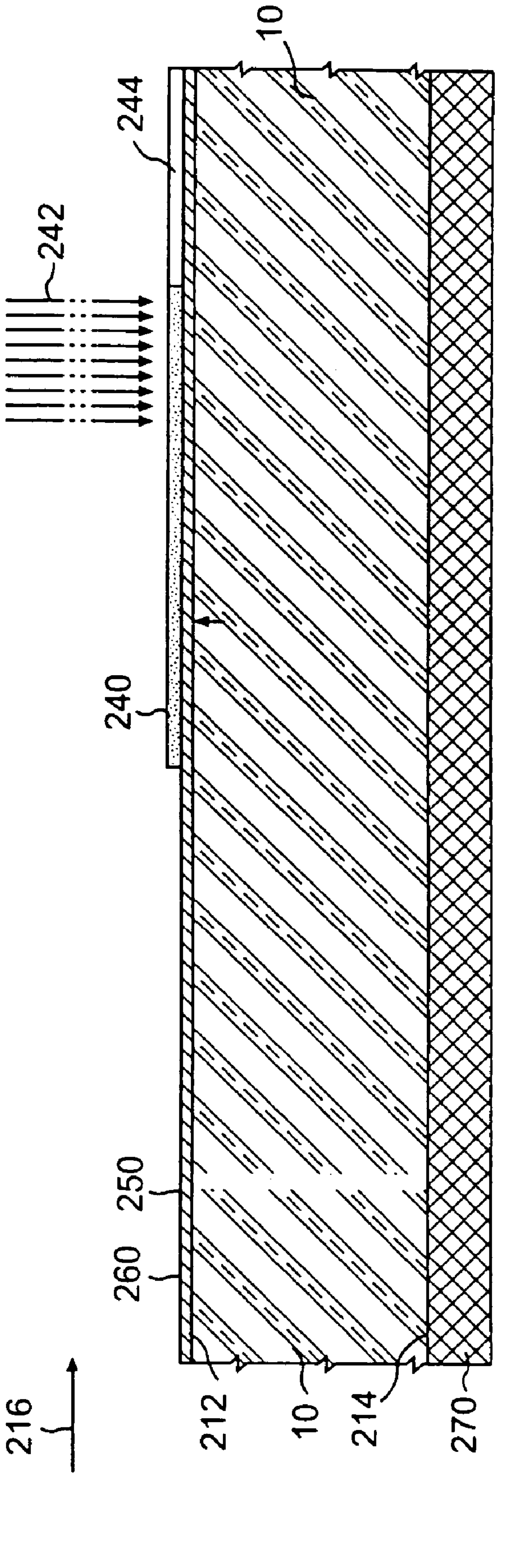
FIG. 11 is a cross-section view of a length of a web for flexible packaging material according to an embodiment of the present invention.

As shown in FIG. 11, a packaging material 200 consistent with one illustrative embodiment includes a substrate 10 having a top side 212 and a bottom side 214, and a lacquer coating 240 applied on top side 212 of substrate 10. In the illustrated embodiment of FIG. 11, packaging material 200 is schematically shown to go through a particle beam processing device 100 of this embodiment in the direction of arrow 216. Substrate 10 is generally in the form of a continuous web. However, substrate 10 may also be in the form of a sheet.

Lacquer coating 240, such as an over-print varnish (OPV), is formulated for exposure to highly accelerated particles schematically illustrated and referred to as arrows 242. Particles 242 may be electron beams such as those electrons generated by particle beam generating assembly 110. When exposed to electron beams 242, lacquer coating 240 is treated by going through a chemical reaction, i.e., a polymerization process in which it is physically transformed from a liquid state to a solid state (illustrated in FIG. 11 as reference number 244). This polymerization process is commonly referred to as being a curing process. Advantageously, lacquer coating 240 may be cured theoretically almost instantaneously or practically within approximately a few mili-seconds. For the manufacturers of consumer food products, like chocolate bars, potato chips, candies, dried fruits, etc., where mass quantity production is essential, this is a tremendous breakthrough since packaged products can be quickly shipped to suppliers and consumers.

Lacquer coating 240 serves several purposes, including protecting the ink of a label print 250 from smearing and scratching, providing traction to enable the web to run through the EB machine, and for aesthetic reasons, presenting a high gloss finish to the packaged product. Lacquer coating 240 may be made of a functional group, such as acrylate ester including multifunctional acrylates for free radical polymerization, vinyl ethers, cycloaliphatic diepoxide and polyol systems, for cationic polymerization. The lacquer coating may also include wetting agents and other additives to control coefficient of friction (COF) and import desired functional properties, such as gas and aroma barrier properties.

For example, the following are possible candidates for the multifunctional acrylate:

acrylated polyols with molecular weights from 150 to 600;

polyester acrylates with molecular weights from 1000 to 2000;

polyether acrylates with molecular weights from 200 to 1500;

polyester urethane acrylates with molecular weights from 400 to 2000;

polyurea acrylates with molecular weights from 400 to 2000;

epoxy acrylates with molecular weights from 300 to 1000; and mixtures of multifunctional acrylates.

More particularly, the multifunctional acrylate may include pentaerythritol tetraacrylate, ditrimethylolpropane tetraacrylate, trimethylolpropane triacrylate, glycerol triacrylate, triacrylate ester of tris-t2hydroxy-ethyll isocyanurate, hexanediol diacrylate, and dipentaerythritol hexacrylate, and ethoxylated and propoxylated derivatives thereof.

Lacquer coating 240 may have a normalized thickness (expressed in terms of its mass density) in a range of 0.5–20 grams/m$^2$. In one embodiment, lacquer coating 240 preferably has a thickness in a range of 1–10 grams/m$^2$, and more preferably 2–5 grams/m$^2$.

Also consistent with the principles of one embodiment of the present invention, lacquer coating 240 is preferably treated using the EB machine having a power supply and operating at a voltage of 110 kVolts or below. For one application, the operating voltage of the EB machine may be in a range of 60–110 kVolts, or preferably between 70–110 kVolts, and more preferably between 90–110 kVolts.

Furthermore, lacquer coating 240 may be treated using the EB machine which generates electrons emitting energy in a range of 0.5–10 Mrads to cure lacquer coating 240. In one example, the emitted electron energy is preferably in a range of 1–7 Mrads, or preferably in a range of 2–5 Mrads.

Also consistent with the principles of another embodiment of the present invention, substrate 10 may be made of a material such as polyolefins, including oriented polypropylene (OPP), cast polypropylene, polyethylene and polyethylene copolymer; polystyrene; polyesters, including polyethylene terephthalate (PET), or polyethylene naphthalate (PEN); polyolefin copolymers, including ethylene vinyl acetate, ethylene acrylic acid and ethylene vinyl alcohol (EVOH), polyvinylalcohol and copolymers thereof; polyamides, including nylon, and MXD6; polyimides; polyacrylonitrile; polyvinylchloride; polyvinyl dichloride; polyvinylidene chloride; polyacrylates; ionomers; polysaccharides, including regenerated cellulose; silicone, including rubbers or sealants; natural or synthetic rubbers; glassine or clay coated paper; paper board; craft paper; and metallized films and vapor deposited metal oxide coated polymer films, including $AlO_x$, $SiO_x$, or $TiO_x$.

To provide desired strength to the packaging and to maintain quality of the contents of a packaged product, substrate 10 may have a thickness in a range of 10–200 grams/m$^2$, preferably 30–90 grams/m$^2$, or more preferably 50–70 grams/m$^2$.

Further consistent with the principles of this embodiment of the present invention, substrate 10 may have a barrier layer 260 applied on top side 212 of substrate 10 to maintain a prerequisite condition of the contents of a packaged product. If the contents of the packaged product are foods, such as potato chips, for example, the prerequisite condition may include flavor, freshness, taste, crispness, color, etc.

Barrier layer 260 may be applied by a technique commonly known as vacuum deposition process whereby a layer of, for example, vaporized aluminum, aluminum oxides ($AlO_x$), silicone oxides ($SiO_x$), or other suitable materials is deposited onto substrate 10 to maintain the prerequisite condition of the contents of a packaged product. In a vacuum deposition process using an aluminum oxide, the process also known as a metallization, whereby aluminum is heated to above melting temperature under a vacuum condition in a chamber. A continuous web is run through the vacuum chamber filled with molten aluminum via a series of rollers. Under a controlled condition, the molten aluminum is deposited on either one or both of its surfaces creating a precise thickness of aluminum metallization on the web. This metallization can be seen, for example, as the shiny silver-colored coating on the inner side of a bag of potato chips. In one embodiment, barrier layer 260 may have a thickness in a range of 100–1000 Angstroms.

Label print 250 may be applied directly on top side 212 of substrate 10, usually, but not necessarily, on top of the barrier layer 260. When substrate 10 includes barrier layer 260, label print 250 may be applied after application of barrier layer 260 onto substrate 10. Label print 250 according to this embodiment may be applied as a surface print, as oppose to the reverse printing. Surface printing may be performed using the currently available techniques, such as flexography printing, rotor gravuare printing, offset lithography printing, spray printing, etc. Generally, in a printing zone of the EB machine, continuous sheet of substrate 10 is run through a series of rollers (not shown) to receive the surface printing on its top side 212 by one of those printing techniques. Preferably, in the flexible packaging industry, printing is done by a flexography method. Label print 250 may be any types of well known flexography inks, including solvent based, water based, and electron beam curable ink, such as Unicure™ available from Sun Chemicals Ink of Northlake, Ill. This embodiment further anticipates that lacquer coating 240 and label print 250 on substrate 10 may be simultaneously treated when they pass through the particle beam processing device 100.

Yet further consistent with the principles of this embodiment of the present invention, substrate 10 may have a radiation labile layer defined as a layer of material susceptible to radiation damage. Radiation labile layer may be a sealing layer 270, applied on bottom side 214 of substrate 10. Sealing layer 270 is provided to facilitate sealing of the packaging material and to give structure to the packaging without being chemically altered by the radiation from the particle beam processing device 100. To give structure to the packaging, sealing layer 270 may be provided with a thickness in a range of 5–50 grams/m$^2$, preferably 8–35 grams/m$^2$, more preferably 12–25 grams/m$^2$, or most preferably 15–20 grams/m$^2$. Sealing layer 270 may be applied to bottom side 214 of flexible substrate 210 by any conventional means, such as an extrusion method.

In a consumer food producing company, after lacquer coating 240 has been treated, substrate 10, commonly in a form of a continuous web, goes through a cutting process whereby the continuous sheet is first folded to become a continuous tube, then cut to size to make individual bags, arranged in an assembly line to be sealed on one end of the bags. In the cutting process, continuous sheet of substrate 10 may be run through various rollers to make a continuous U-shaped sheet so that sealing layers 270 are on two inner legs of the U-shaped sheet facing each other. The tips of the legs of the U-shaped sheet may then be sealed to make the continuous tube ready for cutting to individual bag sizes. Then, the assembly line of individual bags goes through a filling process whereby contents of the packaging are filled into the individual bags, and each of the individual bags is sealed on the other end to close the packaging. It is also possible to provide substrate 10 in a form of individual sheets, either already cut to size or ready to be cut to size.

Sealing layer 270 may be made of a material suitable for sealing a packaged product, such as by heat sealing, cold sealing, or other equivalent sealing processes. When sealing layer 270 is provided for heat seal layer, sealing layer 270 may be made of polymers preferably having a melting point at a temperature range of 100–150 degrees Celcius. Examples of such polymers are polyethylene, polyvinylacetate, ethylene propylene copolymer, terpolymer ethylene acrylic acid, metallocene, ionomer, and combination thereof. For bagging snack foods, like potato chips, for example, sealing layer 270 may be made of polyethylene or polyethylene/polypropylene copolymer terploymer having a melting temperature range of 110–140 degrees Celcius.

Alternatively, sealing layer 270 may be provided for cold seal layer to cold seal the packaging. In one embodiment, a cold seal adhesive may be applied to the substrate. For cold seal coating, sealing layer 270 may be made of natural rubber, polyamides, and combination thereof.

The following comparative examples present several applications of the web packaging material according to the present embodiment in the current market, including stand-up pouch packaging, confectionary packaging, and snack food packaging. As can be seen from the following examples, the web packaging material of the present illustrative embodiment improves the currently available packaging material by offering cost savings, better quality product, and environmental consciousness. The present illustrative embodiment accomplishes these improvements by using less raw material and using a low voltage EB machine to cure the packaging material. For exemplary purposes, Examples 8–10 discuss the polymers in terms of their normalized thickness measured in grams/m$^2$.

EXAMPLE 8

Stand-Up Pouch Packaging

Stand-up pouch packaging is used to package, for example, cookies, nuts, dried fruits, etc. In today's market, packaging for stand-up pouches is made in a laminate form, i.e., at least two layers of polymers being laminated to sandwich an adhesive layer. The following is an example of stand-up pouch packaging in the current market:

| Polymer Laminates in Current Market | Thickness (in grams/m$^2$) |
|---|---|
| Polyester type (PET) | 16 |
| Reverse printing | — |
| Adhesive (extruded polyethylene) | 12 |
| Metallized oriented polypropylene (OPP) | 15 |
| Adhesive (extruded polyethylene) | 12 |
| Low density polyethylene | 30 |
| Total | 85 |

A packaging material made consistent with the principles of this embodiment of the present invention may have the following construction for a stand-up pouch packaging:

| Packaging Material of the Present Embodiment | Thickness (in grams/m$^2$) |
|---|---|
| Over-print varnish (OPV) | <5 |
| Surface printing | — |
| Metallized oriented polypropylene (OPP) | 50 |
| Extruded polyethylene (PE) coating | 20 |
| Total | <75 |

In the exemplified embodiment, over-print varnish of lacquer coating 240 is about 3–5 grams/m$^2$ thick and is curable with an EB machine at least 2.0 Mrads and operating at a range of 80–110 kVolts. It can be seen that the web packaging made according with the principles of this embodiment of the present invention uses less raw material than the conventional stand-up pouch packaging by about 10 grams/m$^2$, which is a raw material saving of almost 15–20%. In addition, the web packaging made according with the principles of the present embodiment offers energy and cost savings related to reducing several operating or processing steps.

EXAMPLE 9

Confectionary Packaging

Confectionary packaging is used to package, for example, candies and candied products. The following is an example of confectionary packaging in the current market:

| Polymer Laminates in Current Market | Thickness (in grams/m$^2$) |
|---|---|
| Oriented polypropylene (OPP) | 18 |
| Reverse printing | — |
| Water-based adhesive | 2 |
| Oriented polypropylene (OPP) | 28 |
| Cold seal adhesive pattern coated | — |
| Total | 48 |

A packaging material made consistent with the principles of this embodiment of the present invention may have the following construction for a confectionary packaging:

| Packaging Material of the Present Embodiment | Thickness (in grams/m$^2$) |
|---|---|
| Over-print varnish (OPV) | <5 |
| Surface printing | — |
| Oriented polypropylene (OPP) | 35 |
| Cold seal adhesive pattern coated | — |
| Total | <40 |

In this example, over-print varnish of lacquer coating 240 is curable with an EB machine at least 2.0 Mrads and operating at a range of 80–110 kVolts. It can be seen that the web packaging made according with the principles of the present embodiment uses less raw material than the conventional packaging, a material cost saving of about 8 grams/m$^2$ or 10–15%. In addition, the web packaging made according with the principles of the present embodiment offers energy and cost savings related to reducing several operating or processing steps.

EXAMPLE 10

Snack Food Packaging

Snack food packaging is used to package, for example, potato chips, corn chips, and pretzels. The following is an example of snack food packaging in the current market:

| Polymer Laminates in Current Market | Thickness (in grams/m$^2$) |
|---|---|
| Oriented polypropylene (OPP) | 18 |
| Reverse printing | — |
| Adhesive (extruded polyethylene) | 15 |
| Metallized heat sealable OPP | 18 |
| Total | 51 |

A packaging material made consistent with the principles of the present embodiment may have the following construction for a snack food packaging:

| Packaging Material of the Present Embodiment | Thickness (in grams/m$^2$) |
|---|---|
| Over-print varnish (OPV) | <5 |
| Surface printing | — |
| Metallized oriented polypropylene (OPP) | 18 |
| Extruded PE for heat sealing and bulk | 18 |
| Total | <41 |

In this example, over-print varnish of lacquer coating 240 is also curable with an EB machine at 2.0 Mrads and operating at a range of 80–110 kVolts. It can be seen that the web packaging made according with the principles of this embodiment of the present invention uses less raw material than the conventional packaging, a cost saving of about 10 grams/m$^2$ or 15%. In addition, the web packaging cured with the EB machine according with the principles of the foregoing embodiment of the present invention offers substantial energy savings as compared with the conventional oven operation used in the current market.

The process described above offers several advantages, such as, the particle beam processing happens virtually instantaneously, commonly operates at room temperature and produces no emissions or air pollution since particle beam coating materials are 100% solids. In addition, the coatings do not contain harmful solvents or volatile organic compounds. In addition, energy costs to operate EB is substantially lower than operating ovens used today.

It has been shown (for example, with reference to FIGS. 5 and 7) that a thinner foil 142 tends to absorb less energy than thicker foils when using a lower operating voltage, thereby resulting in higher efficiency and throughput. A lower operating voltage enables use of a smaller transformer and less overall equipment, resulting in more compact and less expensive EB equipment.

As mentioned above, one application for low voltage EB equipment is instantaneous curing of laminating adhesives (see above Examples 3 and 8–10). Using an EB particle beam processing device 100 to instantly cure a laminating adhesive removes the 12 hour to 7 day WIP (work in process) inventory required when using time-cured solvent, water, or 100% solids adhesives, translating into cost savings to the manufacturer. Using EB curing also avoids the use of potentially toxic isocyanate chemistry associated with some of the incumbent chemistry. In addition, instantaneous curing provides other extra benefits such as real time quality control and less waste. Accordingly, using an EB device to instantaneously cure an adhesive that joins two similar or dissimilar substrates (such as plastic films or a plastic film with an inorganic layer like aluminum foil) is an important EB application.

It has been shown that operating at 110 kV works quite well for joining "duplex" structures in which an adhesive joins two films or a film to an inorganic layer like aluminum foil. There are certain duplex and other structures involving thicker materials, however, where a higher operating voltage is may be required to adequately cure an adhesive layer, or layers, beneath one or more material layers. A triplex structure, where two separate adhesive layers are used to join three material layers, is an example of a structure that may require a higher operating voltage to cure both adhesives. Certain stand-up pouch applications that require thicker packaging utilize a triplex structure, such as packaging for liquid drinks, snacks, etc., as well as non-food applications like motor oil, fertilizer, etc. The following is an example of a triplex construction:

PET\Print\Adhesive\Aluminum\Adhesive\LDPE

Without the use of EB curing, the following method can be used to make the above-mentioned structure:

Step 1: Reverse print the PET (Polyester) film.

Step 2: Laminate the printed film to aluminum foil using a time-cured adhesive.

Step 3: Wait 24 hours for adhesive to cure.

Step 4: Laminate the PET\Aluminum laminate to LDPE (low density polyethylene) with time cured adhesives.

Step 5: Wait 24 hours in non-food applications, or wait up to 7 (or more) days for food applications.

Using an EB device 100 to instantaneously cure the laminating adhesives, one could complete the foregoing triplex structure in the following steps:

Step 1: Reverse print the PET film.

Step 2: Laminate the triplex PET\Aluminum\LDPE structure using EB laminating adhesives.

Step 3: EB cure the entire triplex structure in-line. The structure can be used without delay since EB cures the adhesive instantly.

It can be seen that in making a triplex structure, for example, EB curing simplifies the manufacturing process by reducing the operating steps and enables the structure to be used or shipped the same day resulting in significant cost savings. Due to the greater thickness of the triplex structure, however, higher operating voltages may be needed to adequately cure the second adhesive layer. More generally, when a material layer to be treated, such as adhesive, is a layer within a structure (duplex, triplex, or other) in the thickness range of about 30 to 50 grams/m$^2$, an operating voltage of 110 kV may not adequately treat the layer. The following example shows that a higher operating voltage (125 kV versus 110 kV) provides better results for a "triplex" structure.

EXAMPLE 11

The following triplex structure was made using EB laminating adhesives:

PET\Print\Adhesive\Aluminum\Adhesive\LDPE

The structure was made using both a 110 kV operating voltage and a 125 kV operating voltage. The following table shows the results:

| | Thickness (grams/m$^2$) | 110 kV (Mrad) | 125 kV (Mrad) |
|---|---|---|---|
| PET (12.5 microns) | 17.5 | | |
| Reverse Print | 2.0 | | |
| Adhesive 1 | 2.0 | | |
| Sub-total 1 | 21.5 | 2.65 | 2.95 |
| Aluminum (8 microns) | 21.6 | | |
| Adhesive 2 | 2.0 | | |
| Sub-total 2 | 45.1 | 1.80 | 2.40 |
| LDPE (50 microns) | 47.0 | | |
| TOTAL | 92.1 | 0.30 | 0.87 |

The EB laminating adhesives 1 and 2 used were an acrylate ester from Northwest coatings (Product # NWC19140). Adhesive 1 was applied on a reverse printed Polyester (PET) film by flexo method. This was then laminated to 8 micrometer aluminum foil. Adhesive 2 was applied to a side of the polyethylene (LDPE) film, which side was then laminated to the exposed side of the aluminum foil to form the triplex structure.

Figure 12:
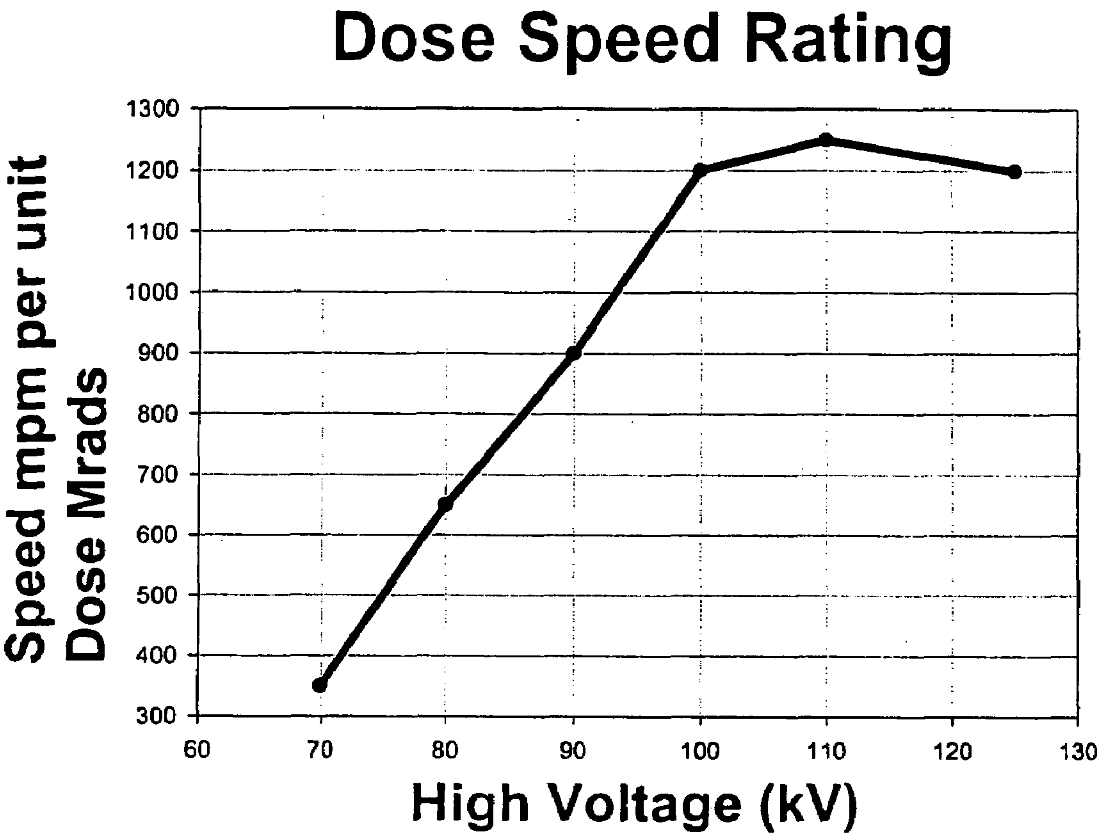
FIG. 12 is a chart of a dose speed rating of a particle beam processing device according to another illustrative embodiment.

The entire triplex laminated structure was then EB cured using a particle beam processing device 100 (FIG. 1), such as the EZCure™ I 110/75/1200 unit from Energy Sciences, Inc. of Wilmington, Mass. The processing device utilized a 10 micron titanium foil 142. FIG. 12 shows the dose speed rating of the EZCure™ processing device used. As shown in FIG. 12, the device delivers 1 Mrad at 1200 mpm (meters per minute) at 125 kV, and 3.0 Mrads at 400 mpm, a speed typically desired for such packaging applications.

The triplex structure was exposed to the electron beam such that the PET layer was facing the electron beam and the electrons traveled through the PET layer (and the aluminum layer for adhesive 2) to cure adhesives 1 and 2. One sample of the structure was cured using an operating voltage of 110 kV with a surface dose of 3.0 Mrad, while a second sample was cured at an operating voltage of 125 kV with a surface dose of 3.0 Mrad.

It was found that at both operating voltages, adhesives 1 and 2 appeared cured, and the LDPE layer had no detrimental effects on heat sealability or any other physical property. However, it was found that adhesive 2 cured at 110 kV had a slightly higher odor than adhesive 2 cured at 125 kV. The increased odor in the laminate cured at 110 kV is due to the EB dose received by the adhesive layer, which is illustrated in the above table and in FIG. 13.

From the above table one can observe that at an operating voltage of 110 kV and a surface dose of 3.0 Mrads, adhesive 1 receives a dose of 2.65 Mrads, while adhesive 2 receives a dose of only 1.8 Mrads causing the material to be slightly under-cured, thereby creating an odor. Further, this dose is lower than the required 2.4–2.5 Mrads recommended by the adhesive supplier for the packaging to comply with food law. At 125 kV adhesives 1 and 2 receive a does of 2.95 and 2.4 Mrads, respectively, both high enough to adequately cure adhesives 1 and 2 (thereby reducing off-odor to a non-detectable level) and to comply with FDA requirements.

Figure 13:
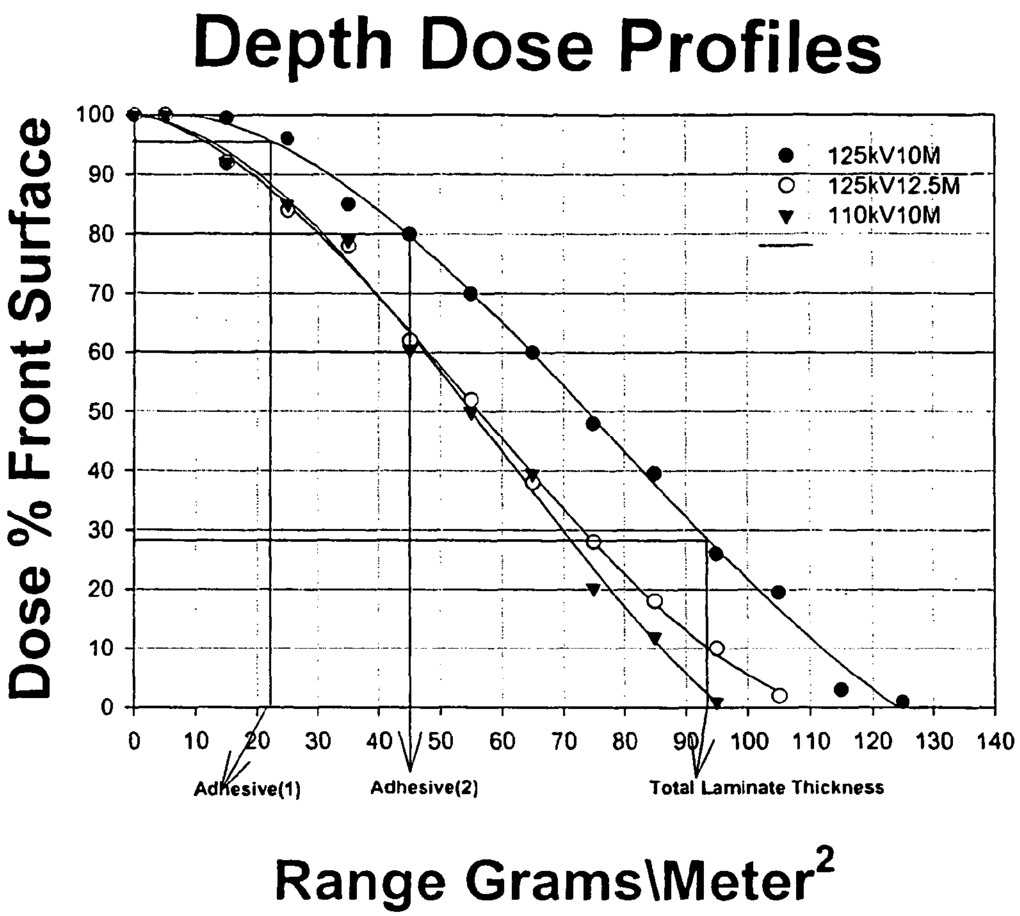
FIG. 13 is a chart of depth dose profiles using various foil thicknesses and operating voltages.

FIG. 13 shows the depth dose profiles for the 110 kV and 125 kV operating voltages. Also shown is the dose profile using an operating voltage of 125 kV and a foil of 12.5 microns. As seen in the graph of FIG. 12, the dose received by adhesive 2 is essentially the same (60% of the surface dose) for both 110 kV with 10 micron foil and 125 kV with 12.5 micron foil. This results in under-curing of adhesive 2, while using 125 kV with 10 micron foil results in adhesive 2 receiving 80% of the surface dose. Therefore, for structures (single layer, duplex, triplex, etc.) in which curing is needed in some portion or all of the range of thickness from about 20 to 90 grams/m$^2$, and more particularly 30 to 50 grams/m$^2$, e.g., for adhesive 2 in the foregoing example, operating voltages greater than 110 kV, e.g., 125 kV, are appropriate and even required. It should be noted that in addition to such curing of a layer of material embedded within the structure, a surface layer, such as lacquer, or a layer from 0 to 20 grams/m$^2$ could be simultaneously treated.

It will be apparent to those skilled in the art that various modifications and variations can be made in the particle generating assembly, foil support, processing zone, and process control system, as well as the materials chosen for the web packaging material, and the materials chosen for the thin foil, the filaments or particle generating components, and in construction of the particle beam processing system as well as other aspects of the invention without departing from the scope or spirit of the invention. For example, although an example of curing a triplex structure has been shown, the invention is not limited to curing any particular structure, and is also applicable to, for example, single layer, duplex, four layer, five layer, structures, etc.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims and their equivalents.

We claim:

1. A method for treating a material with a particle beam processing device, comprising:

providing a particle beam generating assembly including at least one filament for creating a plurality of particles;

applying an operating voltage greater than about 110 kV to the filament to create the plurality of particles;

causing the plurality of particles to pass through a thin foil having a thickness of about 10 microns or less; and treating a material with the plurality of particles, wherein the material is a multi-layered structure.

2. The method of claim 1, wherein the operating voltage is about 125 kV.

3. The method of claim 1, wherein the foil thickness is about 10 microns.

4. A material made by the method of claim 1.

5. The method of claim 1, wherein the structure includes an adhesive to be cured by said plurality of particles.

6. The method of claim 5, wherein the adhesive joins together first and second material layers.

7. The method of claim 6, wherein the structure further includes a second adhesive to be cured by said plurality of particles and to which a third material layer is joined.

8. The method of claim 7, wherein the first material layer is PET.

9. The method of claim 8, wherein the second material layer is aluminum foil.

10. The method of claim 9, wherein the third material layer is LDPE.

11. The method of claim 7, wherein the first and second adhesives are cured at the same time.

12. A method for treating a material with a particle beam processing device, comprising:

providing a particle beam generating assembly including at least one filament for creating a plurality of particles;

applying an operating voltage greater than about 110 kV to the filament to create the plurality of particles;

causing the plurality of particles to pass through a thin foil having a thickness of about 10 microns or less; and treating a material with the plurality of particles, wherein a layer within the range of about 20 to 90 grams/m$^2$ of the material is treated with the plurality of particles.

13. The method of claim 12, wherein the layer is within the range of about 30 to 90 grams/m$^{2.}$

14. The method of claim 13, wherein the layer is within the range of about 30 to 50 grams/m$^2$.

15. A method for treating a material with a particle beam processing device, comprising:

providing a particle beam generating assembly including at least one filament for creating a plurality of particles;

applying an operating voltage greater than about 110 kV to the filament to create the plurality of particles;

causing the plurality of particles to pass through a thin foil having a thickness of about 10 microns or less; and treating a material with the plurality of particles, wherein the material Is a multi-layer structure, and at least two layers are cured by the plurality of particles.

16. The method of claim 15, wherein the at least two layers are within the range of 0 to 90 grams/m$^2$ of the multi-layer structure.

17. The method of claim 1, wherein the foil is made of titanium.

18. The method of claim 1, wherein treating the material with a plurality of particles causes a chemical reaction in the material.

19. The method of claim 1, wherein treating the material with a plurality of particles causes a physical reaction in the material.

20. The method of claim 18, wherein the chemical reaction is at least one of sterilization, polymerization, and crosslinking.

21. A multi-layered material comprising:

a first material layer;

a second EB cured adhesive layer;

a third material layer;

a fourth EB cured adhesive layer; and a fifth material layer.

22. The material of claim 21, wherein the fourth EB cured adhesive layer is within the range of 20 to 90 grams/m$^2$ of the material.

23. The material of claim 21, wherein the fourth EB cured adhesive layer is within the range of 30 to 50 grams/m$^2$ of the material.

* * * * *